(12) United States Patent
Brock et al.

(10) Patent No.: US 6,929,393 B1
(45) Date of Patent: Aug. 16, 2005

(54) ASPHALT PRODUCTION PLANT

(75) Inventors: J. Donald Brock, Chattanooga, TN
(US); Herbert E. Jakob, Chattanooga,
TN (US); R. Ronald Collins,
Mansfield, GA (US); Michael Barrett,
Lula, GA (US); **Thomas Scott
Cloninger, Chattanooga, TN (US); M.
Earl Edwards, Jr.**, Trenton, GA (US)

(73) Assignee: Astec, Inc., Chattanooga, TN (US)

( * ) Notice: Subject to any disclaimer, the term of this
patent is extended or adjusted under 35
U.S.C. 154(b) by 219 days.

(21) Appl. No.: 10/458,144

(22) Filed: Jun. 9, 2003

Related U.S. Application Data

(63) Continuation-in-part of application No. 09/992,169, filed on Nov. 14, 2001, now Pat. No. 6,575,303, which is a continuation-in-part of application No. 09/758,992, filed on Jan. 16, 2001, now Pat. No. 6,581,780, and a continuation-in-part of application No. 09/521,030, filed on Mar. 7, 2000, now Pat. No. 6,318,193, which is a continuation-in-part of application No. 09/168,922, filed on Oct. 8, 1998, now Pat. No. 6,062,093.

(51) Int. Cl.⁷ .............................................. B28C 7/00
(52) U.S. Cl. ......................... 366/16; 366/18; 366/22; 366/140
(58) Field of Search ........................ 366/6, 8, 16, 17, 366/18, 22, 140, 141

(56) References Cited

U.S. PATENT DOCUMENTS

| | | | | |
|---|---|---|---|---|
| 3,263,971 A | * | 8/1966 | Farnham | 366/16 |
| 3,304,065 A | * | 2/1967 | Eaton | 366/18 |
| 3,439,800 A | * | 4/1969 | Tonjes | 209/3 |
| 3,625,488 A | * | 12/1971 | Farnham et al. | 366/18 |
| 3,741,532 A | * | 6/1973 | Farnham et al. | 366/141 |
| 3,809,373 A | * | 5/1974 | Brock | 366/18 |

(Continued)

*Primary Examiner*—Tony G. Soohoo
(74) *Attorney, Agent, or Firm*—Chambliss, Bahner & Stophel, P.C.

(57) ABSTRACT

An asphalt production plant includes an asphalt binder storage tank, a mixer for mixing asphalt binder and aggregate materials, an asphalt binder pumping system for conveying asphalt binder to the mixer and an asphalt binder metering system for controlling the rate of flow of asphalt binder to the mixer. The asphalt production plant also includes a cold feed proportioning system having a plurality of cold feed bins for holding aggregate materials, with each such bin having a discharge opening through which aggregate materials may be discharged, a cold feed conveyor system that extends from beneath the discharge openings for the plurality of bins for conveying aggregate materials to the mixer and an apparatus and system for adjusting the relative proportions of aggregate materials from each of the cold feed bins that are conveyed to the mixer. The asphalt production plant also includes an aggregate sample dryer for removing volatile components from a sample of aggregate materials and an aggregate sampler for obtaining a sample of aggregate material from the cold feed conveyor system and depositing such material in the aggregate sample dryer. A preferred embodiment of the production plant includes an asphalt binder calibration tank, an oven assembly for removing asphalt binder from a sample of asphalt, an asphalt sample collector, an asphalt sample conveyor assembly for conveying a sample of asphalt to the oven assembly and an aggregate gradation assembly for determining the gradation of a sample of aggregate.

20 Claims, 14 Drawing Sheets

U.S. PATENT DOCUMENTS

| | | | |
|---|---|---|---|
| 3,866,887 A * | 2/1975 | Potter | 366/18 |
| 3,880,410 A * | 4/1975 | Heise | 366/22 |
| 4,089,509 A * | 5/1978 | Morton et al. | 366/8 |
| 4,276,093 A * | 6/1981 | Pickermann | 106/281.1 |
| 4,802,139 A * | 1/1989 | Sasaki | 366/16 |
| 5,059,310 A * | 10/1991 | Fischer et al. | 209/237 |
| 5,081,046 A * | 1/1992 | Schneider | 436/139 |
| 5,222,605 A * | 6/1993 | Pogue | 209/239 |
| 5,785,516 A * | 7/1998 | Tanaka | 432/118 |
| 5,947,720 A * | 9/1999 | Kelly | 432/105 |
| 6,000,935 A * | 12/1999 | Regimand et al. | 432/72 |
| 6,054,323 A * | 4/2000 | Troxler et al. | 436/155 |
| 6,062,093 A * | 5/2000 | Brock et al. | 73/864.64 |
| 6,318,193 B1 * | 11/2001 | Brock et al. | 73/864.74 |
| 6,575,303 B1 * | 6/2003 | Brock et al. | 209/238 |
| 6,581,780 B1 * | 6/2003 | Jakob et al. | 209/239 |

* cited by examiner

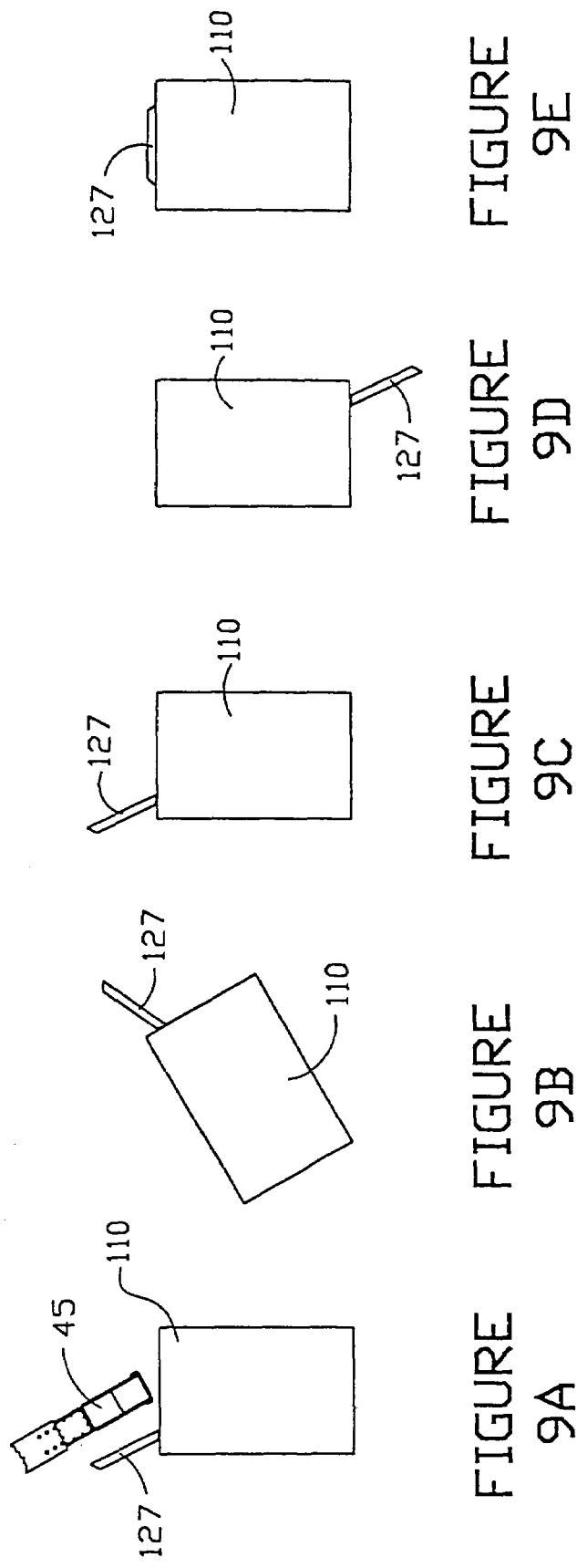

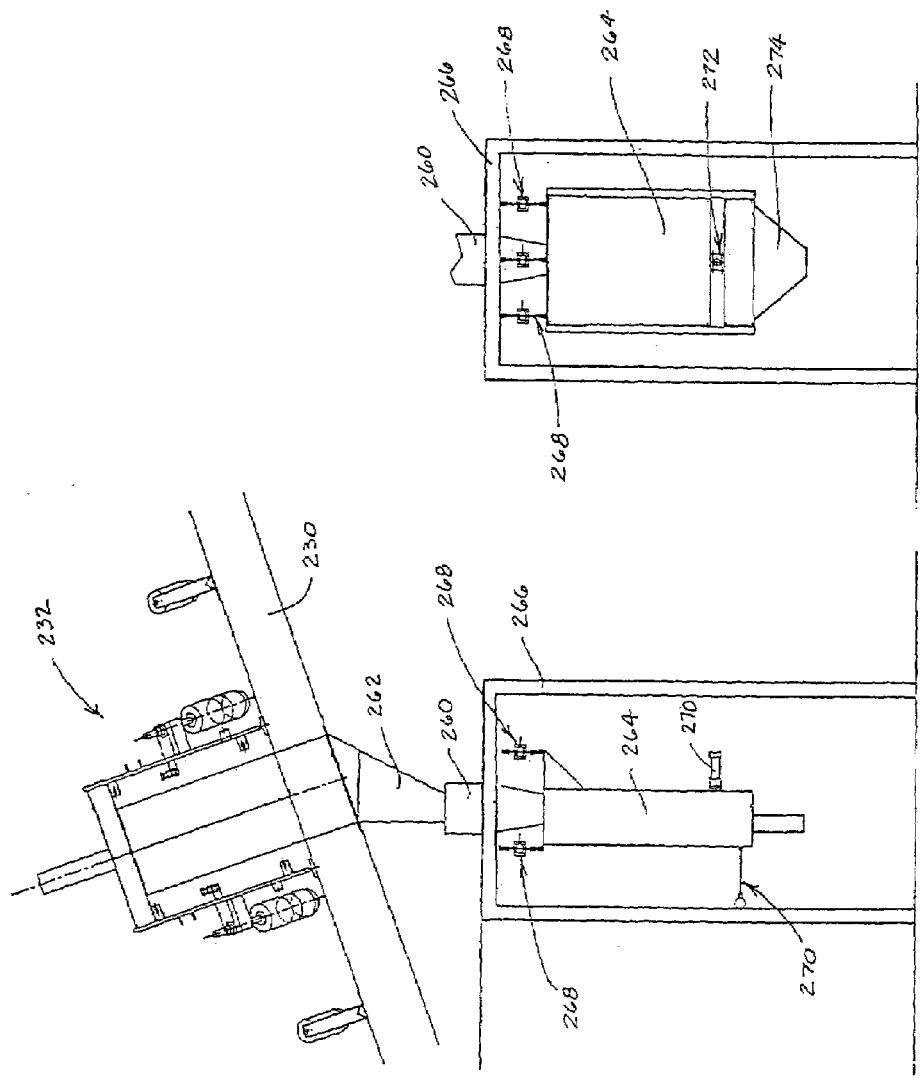

ASPHALT PRODUCTION PLANT

CROSS-REFERENCE TO RELATED APPLICATIONS

This application is a continuation-in-part of the application entitled "Processing A Product Including Aggregate Materials And A Volatile Component" which was filed on Nov. 14, 2001 and assigned Ser. No. 09/992,169, now U.S. Pat. No. 6,575,303, the disclosure of which is fully incorporated herein by reference. Application Ser. No. 09/992,169 is a continuation-in-part of application Ser. No. 09/758,992, now U.S. Pat. No. 6,581,780, which was filed on Jan. 16, 2001 and entitled "Automatic Gradation Unit". Application Ser. No. 09/992,169 is also a continuation-in-part of application Ser. No. 09/521,030, now U.S. Pat. No. 6,318,193, which was filed on Mar. 7, 2000 and entitled "Apparatus For Use In Sampling Aggregate". Application Ser. No. 09/521,030 is a continuation-in-part of application Ser. No. 09/168,922, now U.S. Pat. No. 6,062,093, which was filed on Oct. 8, 1998 and entitled "Method And Apparatus For Sampling Aggregate Material".

FIELD OF THE INVENTION

This invention relates generally to an asphalt production plant for the production of hot mix asphalt. More particularly, the invention relates to an asphalt production plant having items of equipment that may be controlled on the basis of information about the quality and composition of the asphalt product and its various components that is obtained as the product is being produced. In a preferred embodiment of the invention, information about asphalt mix design, binder content and/or the gradation of the aggregate materials used in producing an asphalt product may be obtained prior to production and used to calibrate items of equipment, or it may be obtained at various stages of production and used to control the operation of various items of equipment.

BACKGROUND AND DESCRIPTION OF THE PRIOR ART

It is common in the production of hot mix asphalt to sample the finished product and analyze its composition for quality control purposes. Samples may be taken for analysis to insure that the proper proportions of aggregate materials of various particle sizes, as well as the proper combination of aggregate materials and asphalt binder, are being incorporated into the finished product. Such sampling and analysis is useful and necessary, but it has not been employed in such a way as to provide information that may be used to make real-time adjustments to the operation of the various components of the plant. Indeed, such sampling and analysis as is conventionally practiced may not indicate a problem in the mix design or other parameters until the asphalt product has been delivered to a job site and used. In addition, much of the sampling of the asphalt product (or its constituent components) is carried out by hand, and therefore, may not be representative of the asphalt product being produced. Furthermore, during rainfall and other adverse weather conditions, or when recycled asphalt binder-containing materials are included in the aggregate materials, it may be difficult to analyze the particle sizes of aggregate materials used in the production of asphalt to insure that the proper proportions of the various aggregate materials are being employed.

The surface temperature of hot mix asphalt may be as high as 250–350° F., which makes hand sampling at least uncomfortable and potentially dangerous. Furthermore, a worker who is charged with the responsibility of obtaining a hand sample from a hot mix asphalt truck will not likely be willing and may not be able to spend the time to take sample portions from various locations on the load in the truck bed to insure that he gets a representative sample. Nevertheless, the standard practice for sampling hot mix asphalt from truck transports is to take several portions of a sample from each truck using a flat-bottom scoop or a square-nose shovel. ASTM Designation D 979-96 specifies that at least three approximately equal increments should be taken from each truck load of asphalt sampled. Various state highway departments impose additional requirements on the sampler of asphalt, in an effort to insure that representative samples are obtained. For example, the Georgia Department of Transportation Sampling Procedure GSP-15 specifies that hand samples may be taken only after the "cone" of material in the bed of the truck is first shoveled off to a depth such that the resulting flat area is at least 60% as wide as the truck and at least six inches deep. Wyoming Department of Transportation Sampling Procedure 830.0 requires that for smaller trucks, a sample area must be prepared by removing the top 2–4 inches from each quarter of the load, while for larger trucks, at least two transverse trenches must be excavated across the load in the truck bed. The sample is then removed by pushing the shovel into each cleared area or trench at a 45° angle. Illinois Department of Transportation Sampling Procedure 4.7.1 requires that an equal amount of material is to be taken from locations approximately one foot below the top of each pile in the truck bed, at quarter points around the pile's circumference. Mississippi Department of Transportation Field Testing Procedure TMD-11-77-00-000 requires that at least three samples be taken from specified locations in the truck after first removing the top 2–3 inches of material at each sample point. All of these procedures require that the sampler work for a significant period of time in the bed of the truck atop the load of hot mix asphalt (or adjacent the truck bed from a sampling stand). Complying with such procedures is uncomfortable and may be dangerous, which makes proper sampling problematic.

It is known to use heating devices to facilitate the sampling and analysis of asphalt products. By heating the product to a level sufficient to burn off the volatile asphalt binder, the heating devices effectively isolate the aggregate materials contained in the product for more accurate sampling and analysis of the aggregate material distribution. Examples of such prior art heating devices are contained in U.S. Pat. No. 4,276,093 of Pickermann, U.S. Pat. No. 5,081,046 of Schneider, U.S. Pat. No. 6,000,935 of Regimand, et al. and U.S. Pat. No. 6,054,323 of Troxler. Other asphalt heating devices include rotating and/or tilting containers in which the asphalt may be heated. Such devices are described in U.S. Pat. No. 5,785,516 of Tanaka and U.S. Pat. No. 5,947,720 of Kelly. None of the devices described in these prior art patents, however, is part of an asphalt production plant having items of equipment that may be controlled on a real-time basis as the asphalt product is being produced.

It is also known that the particle size distribution in a quantity of aggregate materials may be determined more-or-less automatically. Thus, for example, U.S. Pat. No. 3,439,800 of Tonjes, U.S. Pat. No. 5,059,310 of Fischer et al. and U.S. Pat. No. 5,222,605 of Pogue describe methods and devices for automatically determining the proportionate amounts of various particle sizes of such a product. Such methods and devices, however, do not contemplate control of equipment such as is employed in the production of asphalt.

It would be desirable if an asphalt production plant could be developed having items of equipment that may be controlled on the basis of information about the quality and composition of the asphalt product and its various components that is obtained as the product is being produced. It would also be desirable if such a plant could be provided in which information about asphalt mix design and the gradation of the aggregate materials used in producing an asphalt product may be obtained at various stages of production and used to control the operation of various items of equipment.

ADVANTAGES OF THE INVENTION

Among the advantages of the invention is that it may be utilized to provide real-time control over the production of asphalt. Such control allows the appropriate proportions of asphalt binder and the various particle sizes of aggregate materials to be maintained in the product within predetermined standards without the production of significant amounts of product that do not meet the necessary standards. Additional advantages of this invention will become apparent from an examination of the drawings and the ensuing description.

Explanation of Technical Terms

As used herein, the term "aggregate materials" refers to crushed stone and other particulate materials that are used in the production of asphalt, such as, for example, crushed limestone and other types of crushed stone, crushed or comminuted recycled asphalt paving materials, crushed, shredded or comminuted shingles and other asphalt binder-containing products, shredded or comminuted mineral and cellulosic fibers, gravel, sand, lime and other particulate additives.

As used herein, the term "asphalt binder" refers to a dark brown to black solid or semi-solid cementious material which gradually liquifies when heated, in which the predominating constituents are bitumens, all of which occur in the solid or semi-solid form in nature or are obtained by refining petroleum, which is used in the production of hot mix asphalt.

As used herein, the term "hot mix asphalt" refers to a bituminous paving mixture that is prepared, using asphalt binder and any of various aggregate materials, in a hot mix asphalt production plant.

SUMMARY OF THE INVENTION

The invention comprises an asphalt production plant which includes an asphalt binder storage tank, a mixer for mixing asphalt binder and aggregate materials, an asphalt binder pumping system for conveying asphalt binder to the mixer and an asphalt binder metering system for controlling the rate of flow of asphalt binder to the mixer. The asphalt production plant also includes a cold feed proportioning system having a plurality of cold feed bins for holding aggregate materials, with each such bin having a discharge opening through which aggregate materials may be discharged, a cold feed conveyor system that extends from beneath the discharge openings for the plurality of bins for conveying aggregate materials to the mixer, and means for adjusting the relative proportions of aggregate materials from each of the cold feed bins that are conveyed to the mixer. The asphalt production plant also includes an aggregate sampler for obtaining a sample of aggregate material from the cold feed conveyor system and an aggregate sample dryer for removing volatile components from a sample of aggregate materials.

In order to facilitate an understanding of the invention, the preferred embodiments of the invention are illustrated in the drawings, and a detailed description thereof follows. It is not intended, however, that the invention be limited to the particular embodiments described or to use in connection with the apparatus illustrated herein. Various modifications and alternative embodiments such as would ordinarily occur to one skilled in the art to which the invention relates are also contemplated and included within the scope of the invention described and claimed herein.

BRIEF DESCRIPTION OF THE DRAWINGS

The presently preferred embodiments of the invention are illustrated in the accompanying drawings, in which like reference numerals represent like parts throughout, and in which:

FIGS. 9a through 9e are sequential schematic side views of the oven assembly of FIG. 8 as it cycles through the various positions of its use according to the invention.

FIG. 10 is front view of the aggregate sampler and the aggregate sample dryer of a preferred embodiment of the invention.

FIG. 11 is a side view of the aggregate sample dryer of FIG. 10.

DESCRIPTION OF THE PREFERRED EMBODIMENTS OF THE INVENTION

Figure 1:
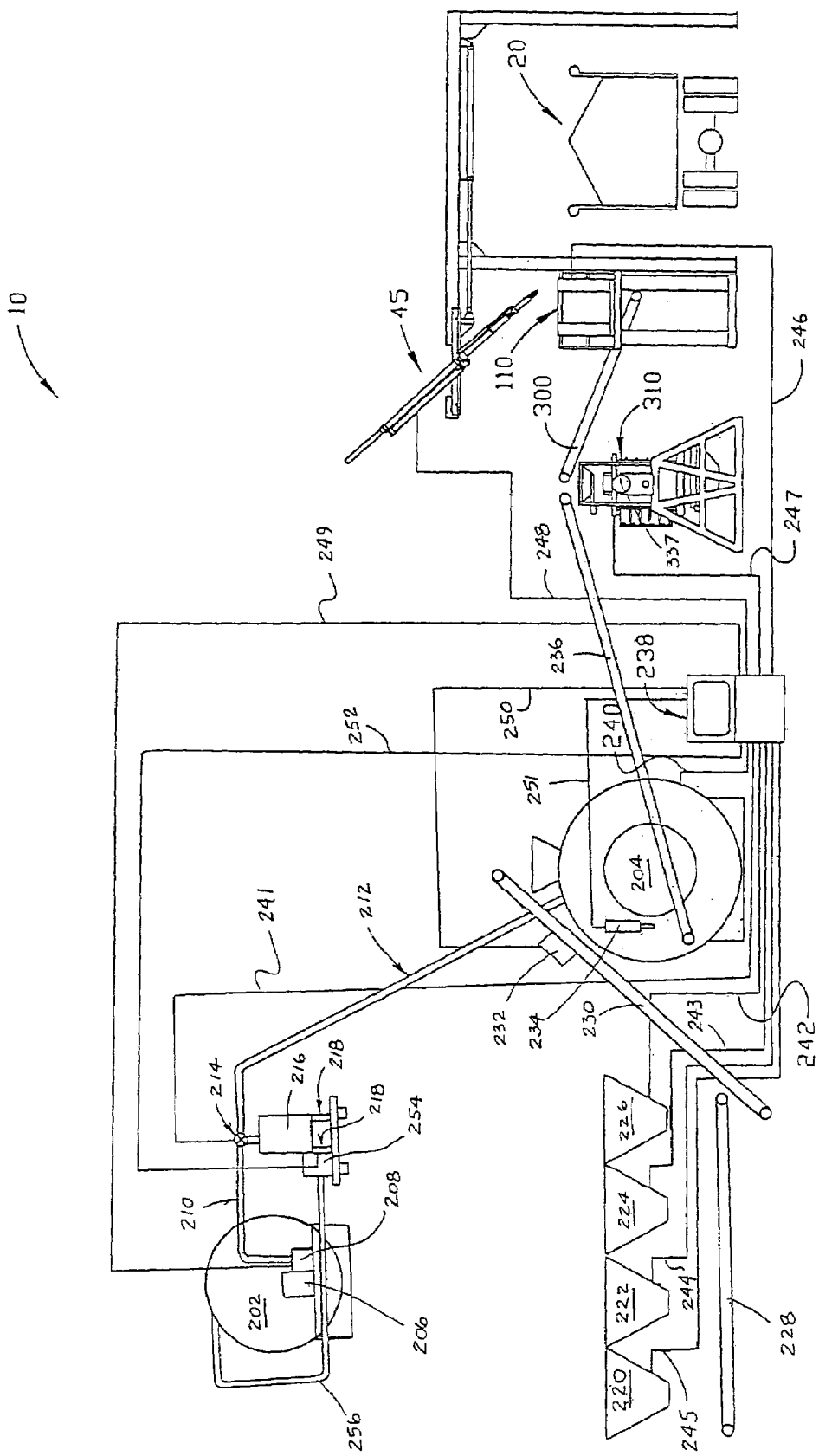
FIG. 1 is a schematic view of a preferred embodiment of the invention.

Referring now to the drawings, the preferred embodiments of the invention are illustrated therein as part of an asphalt production plant. As shown in FIG. 1, the preferred plant 10 includes asphalt sample collector 45, oven assembly 110, gradation assembly 310 and conveyor 300 to convey material removed from oven assembly 110 to the gradation assembly. The preferred asphalt production plant also includes asphalt binder storage tank 202 and drum mixer 204 for mixing asphalt binder and aggregate materials. The preferred binder storage tank includes a heater for maintaining the asphalt binder at the proper temperature for use, and the preferred mixer also heats the aggregate as it is introduced into the mixing chamber in order to volatilize moisture and other volatile components contained therein. Asphalt plant 10 also includes an asphalt binder pumping system for conveying asphalt binder from storage tank 202 to drum mixer 204. The preferred asphalt binder pumping system is comprised of pump 206, metering system 208, asphalt binder transfer pipes 210 and 212, and valve 214 between pipes 210 and 212. When asphalt is being produced in plant 10, asphalt binder is pumped by pump 206 from storage tank 202 through pipes 210 and 212 into drum mixer 204. The volume of flow of asphalt binder from the asphalt storage tank is measured and controlled by metering system 208. Preferably, valve 214 may be operated to direct a flow of asphalt binder from pipe 210 into pipe 212 or from pipe 210 into asphalt binder calibration tank 216. The calibration tank is mounted on load cells 218 and may be used to calibrate the asphalt binder metering system.

Preferred plant 10 also includes a cold feed proportioning system comprised of a plurality of cold feed bins, such as bins 220, 222, 224 and 226, and a cold feed conveyor system comprised of conveyors 228 and 230. Each of the bins is preferably adapted to contain a particular size or gradation of aggregate materials. Each bin has a discharge opening at the bottom thereof which is preferably comprised of a gate that is controlled by a hydraulic (or air) actuator or cylinder (not shown), as is known to those having ordinary skill in the art to which the invention relates. Thus, the discharge openings for each bin may be adjusted to control the amount of aggregate materials of each type that are discharged onto conveyor 228. Conveyor 228 is preferably a variable speed conveyor, and adjustment of the speed of the conveyor may also be utilized to provide a measure of control over the relative proportions of aggregate materials from each of the cold feed bins that are conveyed to mixer feed conveyor 230 and into drum mixer 204. Preferably, the relative proportions of the various aggregate materials that are conveyed to drum mixer 204 are controlled by adjustment of both the discharge openings of the bins and the speed of conveyor 228. Preferred asphalt production plant 10 also includes aggregate sampler 232 for taking a sample of aggregate materials from conveyor 230 and aggregate sample dryer 234 for removing moisture or other volatile components from a sample of aggregate materials obtained by sampler 232. The aggregate sample from which volatile components have been removed may then be deposited onto conveyor 236 and conveyed to gradation assembly 310.

The asphalt production plant of the invention may also employ or include other items that are not shown in the drawings, such as a scalping screen for the cold feed proportioning system, separate cold feed proportioning systems for virgin aggregate materials and recycled materials, a baghouse and other components that are known to those having ordinary skill in the art to which the invention relates.

The preferred asphalt production plant further includes an information processing and machine-controlling device or system such as computer 238 for controlling the operation of the asphalt sample collector, the oven assembly, the gradation assembly, the drum mixer, the discharge openings for the bins, the asphalt binder pumping system, and other components of the plant, including various pumps and conveyors, and for processing information in connection therewith. Computer 238 may be in communication with the various items of equipment by cable systems or by wireless means as are known to those having ordinary skill in the art to which the invention relates. Thus, for example, FIG. 1 illustrates computer 238 as being connected to drum mixer 204 by cable 240, to valve 214 by cable 241, to bin 226 of the cold feed proportioning system by cable 242, to bin 224 by cable 243, to bin 222 by cable 244 and to bin 220 by cable 245. Similarly, computer 238 is connected to oven assembly 110 by cable 246, to gradation assembly 310 by cable 247 and to asphalt sample collector 45 by cable 248. Computer 238 is connected to asphalt binder metering system 208 by cable 249, to aggregate sampler 232 by cable 250, to aggregate sample dryer 234 by cable 251 and to calibration tank load cells 218 by cable 252. In the preferred embodiment of the invention, computer 238 controls the various items of equipment to which it is connected and performs certain calculations and determinations in connection with the operation of some of these items of equipment, as described in more detail hereinafter. Computer 238 may be utilized to control the operation of the various items of equipment by controlling the activation of various switches for activating the items of equipment, or by controlling the activation of cylinders and actuators or other means and mechanisms for moving the various components of the various items of equipment, as hereinafter described in more detail, in a manner known to those having ordinary skill in the art to which the invention relates.

Referring now to the asphalt binder calibration system, when valve 214 is operated to direct asphalt binder from the asphalt storage tank to the calibration tank, the metering system may be set to direct a flow of a measured volume of asphalt binder, such as 1000 gallons, into the calibration tank. As has been mentioned, the calibration tank is mounted on load cells 218, so that the weight of the tank and its contents may be determined. Computer 238 may then determine the net weight of the contents of the calibration tank and convert the weight of the contents to a calculated volume. Preferably, the calibration tank will be weighed prior to deposit of a measured volume of asphalt binder therein to obtain a tare (or empty) weight. This weight will be recorded and saved by the software associated with the controlling computer in order to permit it to determine the net weight of the contents of the calibration tank during the operation of the calibration process according to the invention. By comparing the measured volume of asphalt binder dispensed through the metering system to the calculated volume in the calibration tank, the computer can determine if the asphalt metering system is accurate. If the calculated volume of asphalt binder is not equal to the measured volume, the computer can recalibrate the metering system by communication through cable 252. Once the calibration process is carried out, the asphalt binder in the calibration tank can be pumped by return pump 254 through return line 256 back to the asphalt storage tank.

Among the determinations performed by computer 238 is the determination of the ratios of the weight of the aggregate materials that are retained on any of the screens of gradation assembly 310 or that pass through all of the screens of the gradation assembly to the total weight of the aggregate materials deposited in the gradation assembly by conveyor 236 or by conveyor 300. Preferably, computer 238 is also equipped to compare the ratios of the weights of the various groupings of aggregate materials to a predetermined standard that is stored in its memory for each such ratio. Another function that may be performed by computer 238 is the calculation of the ratio of the weight of the aggregate materials remaining in the oven assembly after heating to remove the asphalt binder component to the weight of the sample of the product transported to the oven assembly by sample collector 45. Computer 238 may also be connected to the various conveyors and other items of equipment illustrated in FIG. 1, although such cable or other connections are not shown in the drawings, and it may be employed to activate these items of equipment at the appropriate times in connection with the production of the asphalt product.

As illustrated in FIGS. 1 through 7, preferred asphalt sample collector 45 is adapted to retrieve a sample of asphalt from a conveyance such as truck 20 and to convey the sample to oven assembly 110. Frame portions 12, 14 and 16, preferably made of steel or other suitable material, generally define a truck zone 18 into which truck 20, containing a load of asphalt 22, may be driven. Of course, the frame of the assembly may be arranged in any convenient configuration, depending on whether the samples are to be taken from trucks, railcars, barges, conveyors or from stationary stockpiles.

Frame portion 16 (shown in partial cutaway in FIG. 2) defines an overhead rail that is suspended over and adjacent to the truck zone. Platform 24 is also located adjacent to the truck zone, and oven assembly 110 is mounted thereon. Platform 24 is elevated by support legs, including legs 28 and 30, which are mounted on base 32. It is also contemplated that the preferred oven assembly may be mounted on the ground (not shown), so long as there is clearance underneath for conveyor 300, thereby eliminating any need for platform 24. Carriage 36 is adapted to ride on overhead rail 16 by means of rollers 38 and 40 between a sampling position over the truck zone (not shown) and a position for depositing the sample in oven assembly 110 (FIGS. 1, 2, 8 and 9A). Hydraulic cylinder 42 is mounted on the overhead rail and the carriage and is provided with cylinder rod 43 that is attached to the carriage so that the cylinder may move the carriage between the sampling position over the truck zone (not shown) and the position for depositing the sample in the oven assembly. Of course, other means and mechanisms for moving the carriage between the sampling and the oven assembly positions as are known to those skilled in the art to which the invention relates, as well as those subsequently developed, are also included within the invention.

Asphalt sample collector subassembly 44, including sample collector 45, is mounted on the carriage at mounting point 46. In one embodiment of the invention, the sample collector subassembly is mounted so as to pivot about mounting point 46. In this embodiment, it is preferred that the sample collector subassembly be mounted to pivot on the carriage so as to permit the sample collector to be inserted into the asphalt product along an axis that is disposed at any angle within the range of about 30° to about 150° from the horizontal. In another embodiment of the invention, the sample collector subassembly may be mounted on carriage 36 at mounting point 46 at a fixed angle, such as at 60° from the horizontal. In another embodiment of the invention, a camera may be mounted on one of the frame portions which define the truck zone, such as on an upper part of frame portion 12 (not shown), so that an operator with a joystick control may remotely operate the asphalt sample collector.

Figure 2:
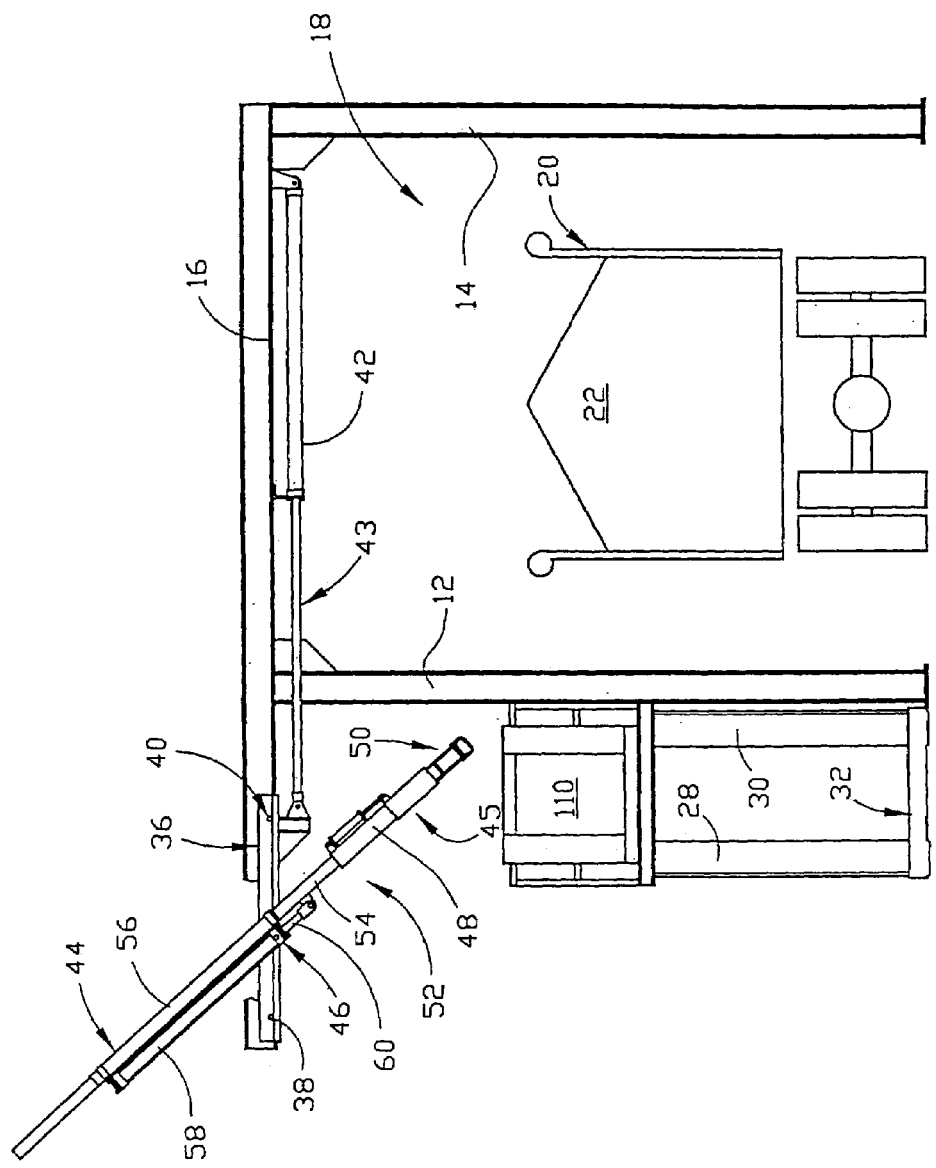
FIG. 2 is a front view of an asphalt sample collector assembly according to the invention that is adapted for sampling of asphalt from a conveyance such as a truck.

FIGS. 3 through 7 illustrate a preferred embodiment of the asphalt sample collector in more detail. As shown therein, asphalt sample collector 45 includes support frame 48 having first end 50 and second end 52. It is generally preferred that the support frame be provided in the form of a length of tubing having a pair of generally planar sides, each of which is disposed generally parallel to the other. The support frame may be provided in a square, rectangular, hexagonal or other convenient cross-section. Preferably, as shown in FIGS. 3–7, frame 48 is a length of square tubing that is made of steel or other suitable material. As shown on FIG. 2, subassembly 44 also includes elongate extension 54, which is attached to the second end 52 of the support frame of collector 45, and boom 56, to which the elongate extension is mounted. These components are also preferably made from steel or other suitable material. Preferably extension 54 is mounted in sliding engagement within boom 56, and is adapted to telescope therefrom. Hydraulic cylinder 58 is attached to boom 56 and provided with cylinder rod 60, which is attached to extension 54, so that cylinder 58 may move extension 54 from a retracted position (shown in FIGS. 1 and 2) to an extended position (not shown) for inserting collector 45 into the asphalt product in the truck. Of course, hydraulic cylinder 58 of the preferred embodiment of the invention that is illustrated in FIGS. 1 and 2 may be replaced by other means for moving the extension with respect to the boom as are known to those having ordinary skill in the art to which the invention relates, or which may be subsequently developed.

Figure 3:
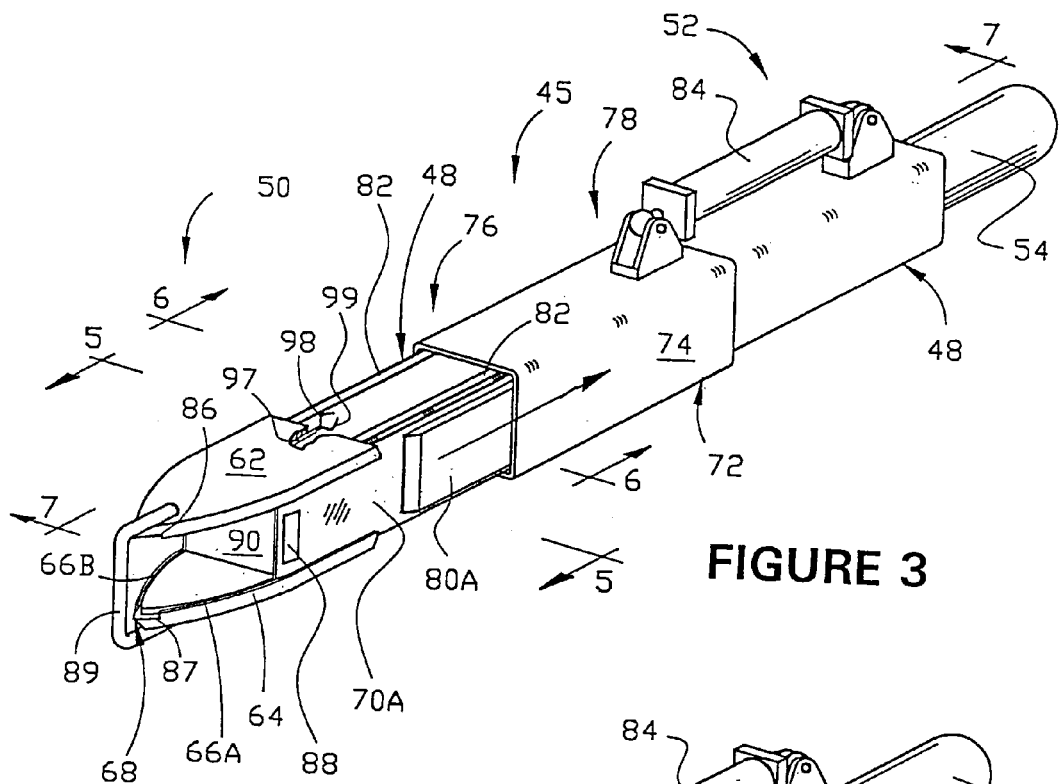
FIG. 3 is a perspective view of the preferred asphalt sample collector that is part of the asphalt sample collector assembly of FIG. 2, showing the closing plate in the open position.
Figure 4:
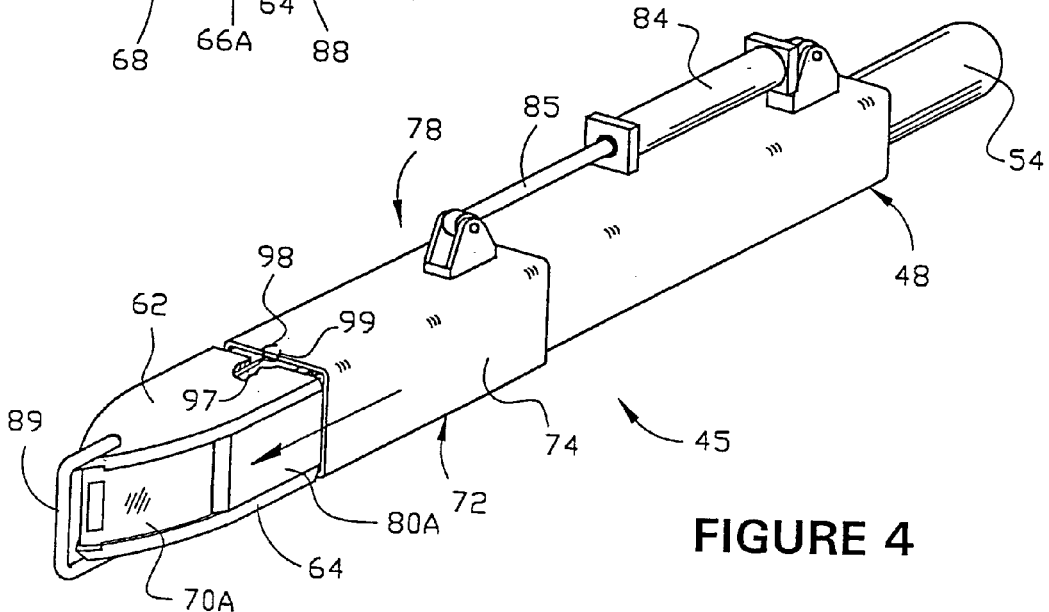
FIG. 4 is a perspective view of the asphalt sample collector illustrated in FIG. 3, but showing the closing plate in the closed position.

As shown in FIGS. 3 and 4, a pair of guide plates 62 and 64 are attached to first end 50 of support frame 48 of asphalt sample collector 45. The guide plates are spaced apart so as to define a collection space therebetween, and at least one of the guide plates is provided with a track that extends generally along the periphery of the collection space. Preferably each of the guide plates is provided with a pair of tracks 66A and 66B so that each track on a guide plate extends generally along one side of the periphery of the collection space to a common termination point 68, and so that the tracks on guide plate 62 (not shown) are generally parallel to the tracks on guide plate 64.

Figure 6:
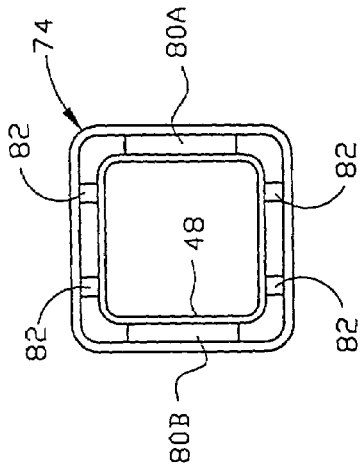
FIG. 6 is a partial cross-sectional view of the asphalt sample collector of FIG. 3, taken along the line 6—6 of FIG. 3.
Figure 5:
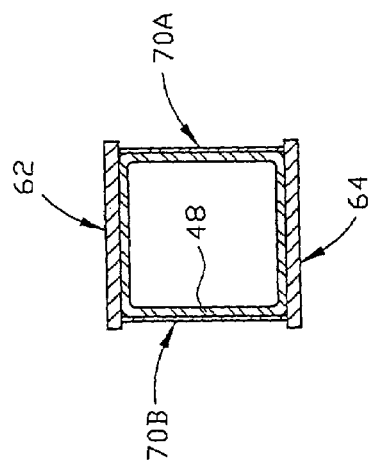
FIG. 5 is a cross-sectional view of the asphalt sample collector of FIG. 3, taken along the line 5—5 of FIG. 3.

Asphalt sample collector 45 also includes at least one flexible closing plate which is disposed between the guide plates and adapted for sliding engagement with the track so that the closing plate may be moved between an open position which exposes the collection space and a closed position which encloses the collection space. Preferably, as shown in FIGS. 3, 4 and 5, a pair of flexible closing plates 70A and 70B (see FIG. 5) are provided. It is also preferred that the closing plates are attached to a carrier which is adapted to move along the support frame. As shown in FIGS. 3, 4 and 6, carrier 72 is preferably comprised of tubing component 74 having a first end 76 and a second end 78, to which (at first end 76) a pair of mounting plates 80A and 80B (see FIG. 6) are attached. Furthermore, the closing plates are preferably attached to the mounting plates on opposite sides of the carrier. Thus, as illustrated in FIGS. 3 and 4, flexible closing plate 70A is attached to mounting plate 80A. It is generally preferred that the carrier be provided in the form of or include a length of tubing having a pair of generally planar sides, each of which is disposed generally parallel to the other. As is the case with respect to the support frame, the carrier tubing component may be provided in a square, rectangular, hexagonal or other convenient cross-section. Preferably, as shown in FIGS. 3, 4 and 6, tubing component 74 of carrier 72 is a length of square tubing that is made of steel or other suitable material. Obviously, if support frame 48 and tubing component 74 of carrier 72 are provided in the telescoping relationship illustrated in the drawings, their shapes must be compatible with such physical arrangement. Furthermore, in order that tubing component 74 may easily slide outside of support frame 48, glide strips 82 are preferably provided between component 74 and frame 48. These glide strips are preferably made of steel or other suitable material and may be applied either to the outer surface of support frame 48, as shown in FIGS. 3 and 6, or to the inner surface of the tubing component of the carrier (not shown).

Carrier 72 is adapted to move along support frame 48 between an open position in which the closing plates expose the collection space and a closed position in which the closing plates enclose the collection space. Preferably, such motion is actuated by hydraulic cylinder 84. As shown in FIG. 4, hydraulic cylinder 84 includes cylinder rod 85 which is attached to second end 78 of tubing component 74 of carrier 72. The cylinder is also preferably attached to support frame 48 so that extension of cylinder rod 85 from cylinder 84 (or retraction of cylinder rod 85 into cylinder 84) will move tubing component 74 of carrier 72 with respect to the support frame between an open position in which the closing plates expose the collection space (FIG. 3) and a closed position in which the closing plates enclose the collection space (FIG. 4). Of course, hydraulic cylinder 84 of the preferred embodiment of the invention that is illustrated in the drawings may be replaced by other means for moving the carrier with respect to the support frame as are known to those having ordinary skill in the art to which the invention relates or which may be subsequently developed.

It is preferred that each of tracks 66A and 66B comprises a groove in the guide plate into which the closing plates may be fitted in sliding engagement, although other track configurations such as a raised rail (not shown) may also be employed. Obviously whatever track configuration is employed, the closing plates will have to be compatible therewith so that sliding engagement will be maintained. It is contemplated that the term "sliding engagement" as used herein to describe the relationship between a closing plate and its associated track includes rolling engagement such as where the track is provided in the form of a raised rail and the closing plate is fitted with wheels that roll on either side thereof. In the preferred embodiment of FIGS. 3 and 4, however, both of the tracks in each guide plate are provided in the form of grooves. In addition, relief openings 86 and 87 are provided in guide plates 62 and 64 respectively (FIG. 3) in order that closing movement of the closing plates may purge the tracks of any sample material that may have accumulated therein when sample collector 45 is plunged into the material to be sampled. This embodiment of the invention also includes a reinforcing strip 88 mounted onto the leading edge of each of the closing plates (only one of which is illustrated in the drawings). These reinforcing strips, which are preferably made of steel, serve to minimize deflection of the closing plates as they close around a sample of material. In addition, nose guard 89, preferably of steel, is mounted to guide plates 62 and 64 adjacent to common termination point 68 in order to minimize deflection of the guide plates and to provide additional protection for the closing plates.

Figure 7:
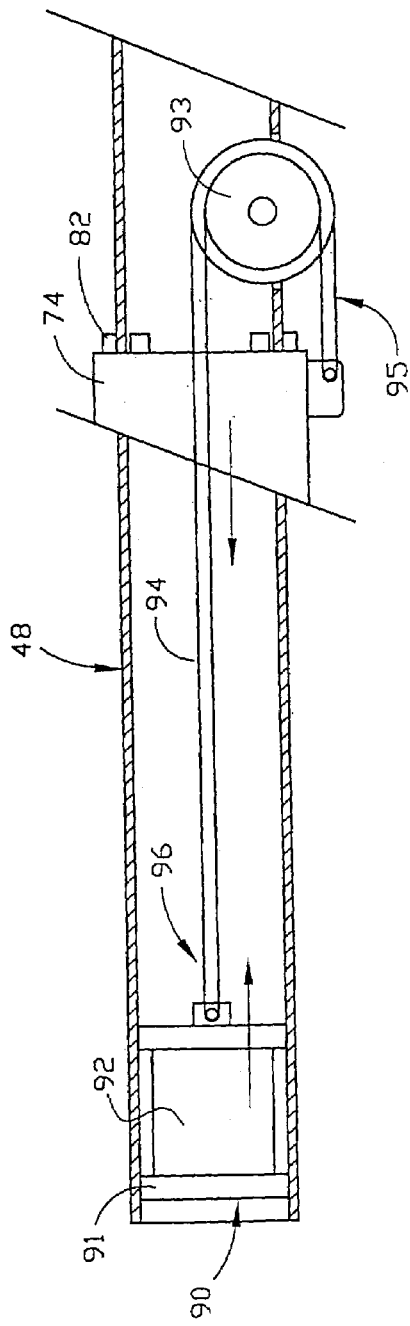
FIG. 7 is a partial cross-sectional view of the asphalt sample collector of FIG. 3, taken along the line 7—7 of FIG. 3.

Another feature of a preferred embodiment of the invention is sample extraction plate 90 that is disposed between the guide plates and which is adapted to push the sample out of the collection space. As illustrated in FIG. 7, it is preferred that the extraction plate be constructed of thick steel plate 91 to which a block or piece of thick tubing 92 is attached for added mass. In the preferred embodiment of the invention, the extraction plate is adapted to conform to the inside shape of support frame 48, and is capable of moving therein so as to push the sample out of the collection space between the guide plates. As shown in schematic form in FIG. 7, it is also preferred that a wheel such as sprocket 93 be mounted within the support frame, and that a belt such as roller chain 94 be provided and disposed around the sprocket. The roller chain has a first end 95 that is attached to the second end 78 of tubing component 74 of carrier 72, and a second end 96 that is attached to the sample extraction plate, or to the block or tubing 92 which is attached to the extraction plate.

Another feature of the preferred embodiment of the invention is heater 97 (FIGS. 3 and 4) that is provided in at least one, and preferably both of the guide plates 62 and 64. Heater 97 is preferably a commercially available cartridge heater that is available from a number of sources, and may be connected to an electrical source by means of wires 98 and 99. The heater may be used to minimize sticking of hot-mix asphalt on the guide plates and other components during the sampling process. In addition, although not shown in the drawings, asphalt sample collector 45 may be provided with a temperature probe that may measure the temperature of the asphalt at the point of sampling.

Figure 8:
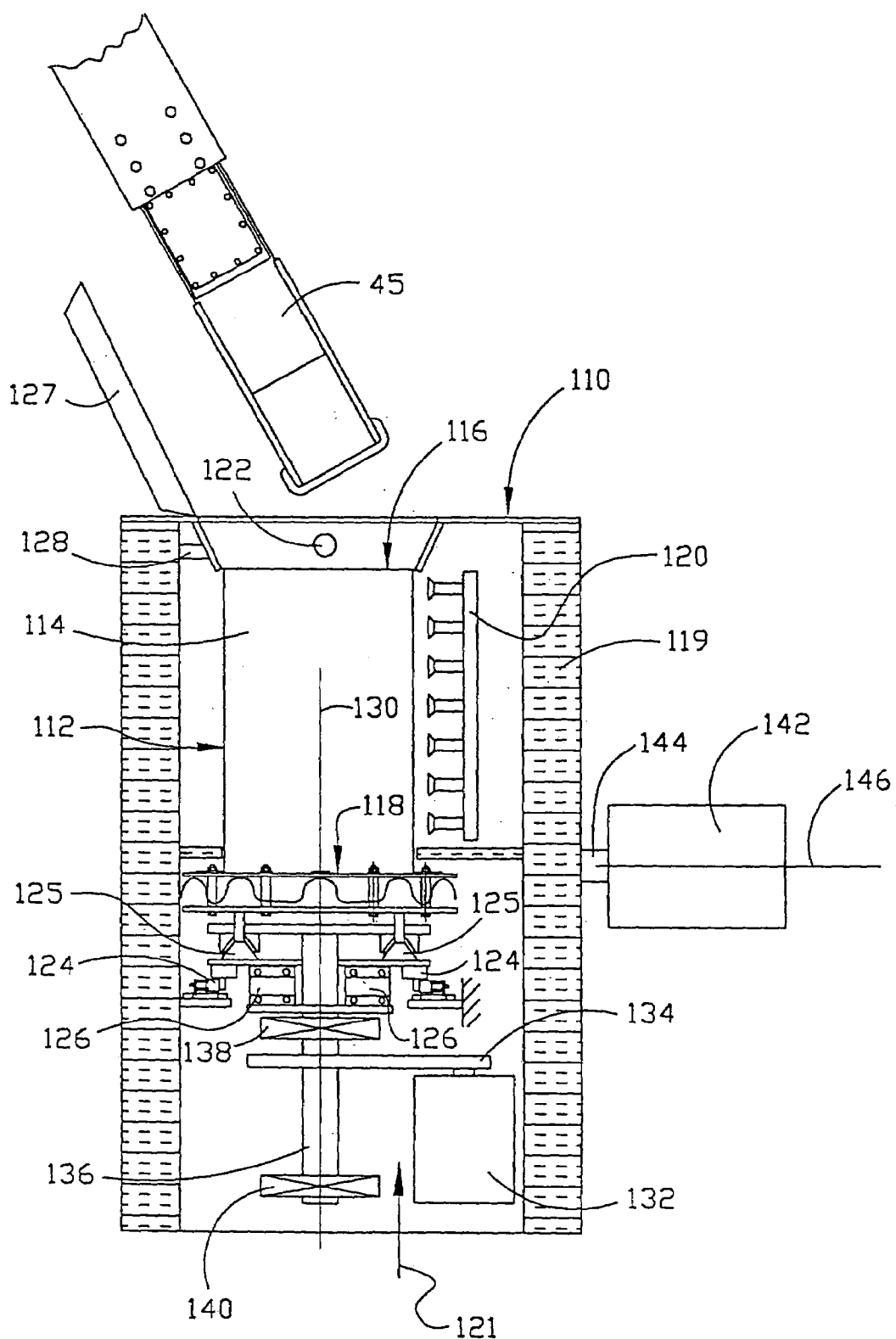
FIG. 8 is a cross-sectional view of the preferred embodiment of the asphalt oven assembly that is a part of the preferred asphalt production plant of FIG. 1.

In the practice of the embodiment of the asphalt sample collector illustrated in FIGS. 1–7, truck 20 is driven into truck zone 18. Carriage 36 with sample collector subassembly 44 mounted thereon is moved by the action of cylinder 42 from the oven assembly position adjacent to the truck zone to a sampling position over the truck zone. Sample collector subassembly 44 is then pivoted (if pivotally mounted on carriage 36) about mounting point 46 to the desired angle, preferably at about 60° from the horizontal. Cylinder extension 54 may then be moved with respect to boom 56 by the action of cylinder 58 from a retracted position to an extended position so as to insert the collector into the product in the truck. Preferably, the collector is inserted so that the collection space is imbedded to a depth of at least about twelve inches in the material in the truck before the closing plates are opened to expose the collection space. This depth is preferred because the outer layers of material in the truck tend to become segregated as the truck is loaded. Consequently, a sample that is more likely representative of the entire load may be obtained from a depth beneath the surface layer of the product. When the collector is placed in the desired position, cylinder rod 85 may be moved by the action of cylinder 84 to move carrier 72 back (along the arrow of FIG. 3) to the open position in which the closing plates expose the collection space. Cylinder extension 54 may then be moved with respect to boom 56 by the action of cylinder 58 so as to insert the collector further into the product in the truck. In the alternative, although not preferred, the collector may be placed in the product with the closing plates in the open position to expose the collection space. As the collector is pushed further into the product (or alternatively, is pushed into the product), extraction plate 90 will be pushed to the back of the collection space and into support tubing 48. Cylinder rod 85 may then be moved by the action of cylinder 84 to move carrier 72 forward (along the arrow of FIG. 4, and to the left as viewed in FIG. 7) to the closed position in which the closing plates enclose the collection space. As this occurs, extraction plate 90 is pulled back (to the right as viewed in FIG. 7) by roller chain 94 within the support tubing, permitting the sample material to enter the collection space. Cylinder 58 may then be actuated to move extension 54 from the extended position to a retracted position to withdraw the collector from the product in the truck. Cylinder 42 may then be actuated to move the carriage to the position for depositing the sample in the oven assembly adjacent to the truck zone. The collector subassembly 44 may be rotated (if necessary) to the preferred sample ejection position, typically at an angle of 45–60° from the horizontal. Cylinder rod 85 may then be moved by cylinder 84 to move the carrier back to the open position in which the closing plates expose the collection space. As this occurs, ejection plate 90 is moved forward under the influence of gravity to push the sample out of the collector and into oven assembly 110 (FIG. 8). Additional samples may then be taken, if desired, from other locations in the truck bed, by changing the angle, the location and/or the depth at which the sample collector is inserted into the asphalt, as well as by moving the truck within the truck zone, if desired.

Oven assembly 110 is adapted to receive a sample of the asphalt product from asphalt sample collector 45 and to remove the volatile asphalt binder therefrom. Oven assembly 110 may also be arranged (although not shown in the drawings) to receive a sample from the sampling mechanism described in copending application Ser. No. 09/758,992, or other sampling means known to those having ordinary skill in the art to which the invention relates. As shown in FIG. 8, preferred oven assembly 110 includes container 112 which defines interior space 114 that is adapted to receive a sample of asphalt. The preferred container is circular in cross-section, but it is also contemplated within the scope of the invention that the container may have a square, rectangular, oval, polygonal or other suitable cross-sectional shape. Container 112 includes receiving end 116 for receiving a sample of the product and closed end 118 opposite said receiving end. Oven assembly 110 includes insulation 119 that is adapted to retain heat in the area of the container. The oven assembly also includes a heat source for heating the sample of the product in the container in order to substantially remove the volatile asphalt binder therefrom. The preferred heat source is a gas burner assembly 120 comprised of a plurality of gas burners that are arranged so as to apply heat directly to the outer surface of container 112. However, it is also contemplated within the scope of the invention that any suitable heat source such as other types of fuel burners, electric heaters, microwave heaters and the like may be used to heat a sample of the product in the container to remove the volatile binder component therefrom. It is preferred that the oven be tilted to an angle of approximately 70° from the vertical and rotated (as hereinafter described in more detail) during heating of the sample in the container. Ambient air may enter the oven during the heating process through openings in the bottom thereof (not shown) in the direction shown by arrow 121 of FIG. 8. Oven assembly 110 is also preferably provided with exhaust burner 122 that is adapted to burn off the volatile exhaust produced by heating the sample of the product.

In addition, oven assembly 110 includes a weighing device, preferably comprised of three scales 124 spaced equally beneath the container (two of which are shown in FIG. 8). Preferably, the container will be weighed prior to deposit of a sample therein to obtain a tare (or empty) weight. This weight will be recorded and saved by the software associated with the controlling computer in order to permit it to determine the net weight of the container during the operation of the oven assembly according to the invention. The weighing device is used, in conjunction with preferred computer 238, in determining the net weight of the container, i.e., the weight of the sample of the product (or portion thereof) contained therein. In the practice of the invention, the weighing device is employed to determine the net weight of the container both before the sample of the product is heated (i.e. when the sample contains the volatile component) and after the sample is heated (i.e. when the volatile component has been removed by heating). The weighing device may be any suitable device for measuring weights, such as one or more scales or load cells. In the preferred embodiment of the invention, oven assembly 110 is also provided with locator cone assembly 125 that is adapted to locate and facilitate the alignment of the container on the weighing device and a plurality of air cylinders 126 that are adapted to raise and lower the container with respect to the weighing mechanism.

Oven assembly 110 also includes door 127 (FIGS. 8 and 9A–9E) that is adapted to move between an open position (FIGS. 8, 9A, 9B, 9C, and 9D) which exposes the interior space of the container and a closed position (FIG. 9E) which substantially closes receiving end 116. Door 126 is preferably hinged on one side, or it may slide from an open position to a closed position, although such an arrangement is not shown in the drawings. If the door is hinged as shown in the drawings, an opening/closing mechanism such as cylinder 128 may be provided to open and close the door as actuated by computer 238. In the alternative, the door may be weighted and arranged on the container so that manipulation of the oven assembly through the positions illustrated in FIGS. 9A–9E (as hereinafter described) will cause the door to be open at positions 9A–9D and closed at position 9E. Oven assembly 110 is also adapted to be rotated about longitudinal axis 130 by a power mechanism such as motor 132 and chain drive 134. Chain drive 134 is connected to a first sprocket (not shown) on the motor shaft and to a second sprocket (also not shown) on shaft 136. Shaft 136 is also attached to container 112 so that rotation of the shaft will cause the container to rotate about axis 130. Bearings 138 and 140 are also mounted on shaft 136 to stabilize and support the shaft during rotation.

A second power mechanism such as motor 142 is provided to tilt the container between an upright position (FIGS. 9A, 9C and 9E) and a dumping position (FIG. 9D) by rotating shaft 144 (which is attached to the oven) about axis 146. In the upright position, receiving end 116 is above closed end 118. In the dumping position, at least a portion of the receiving end is below at least a portion of the closed end.

FIGS. 9A through 9E illustrate sequential side views of the oven as it cycles through the steps of its method of operation. As illustrated in FIG. 9A, the oven is in the upright position with its door open so as to allow the container to receive a sample of hot mix asphalt. Cylinders 126 are retracted to locate the container on the weighing mechanism so that the net weight of the container may be obtained while the oven is in the position of FIG. 9A. Thereafter cylinders 126 are extended to raise the container off the weighing mechanism, and motor 142 may be actuated to tilt the oven, preferably to an angle of approximately 70° from the upright position (as shown in FIG. 9B), which is the preferred position for heating of the sample in the container. Motor 132 is also preferably actuated during heating to rotate the container about axis 130. After heating of the sample in the container, the rotation imparted by motor 132 is stopped and motor 142 is again actuated to tilt the oven back to the upright position, as shown in FIG. 9C. Air cylinders 126 may then be retracted to lower the container onto the weighing mechanism in order to obtain the net weight of the container after heating to remove the volatile binder component. The air cylinders are then extended to raise the container off the weighing mechanism and motor 142 is actuated to rotate the container to a dumping position (preferably approximately 180° from the upright position), as shown in FIG. 9D, in which the remaining components of the product may be dumped from the oven container onto conveyor 300 (FIG. 1). Motor 142 is then actuated once again to tilt the oven back to the upright position, as shown in FIG. 9E.

In the preferred embodiment of the invention, computer 238 is adapted to determine the weight of the volatile binder component in the sample by comparing the net weight of the container before heating to the net weight of the container after heating. The computer will preferably then compare the ratio of the net weight of the container before the sample is heated to the net weight of the container after the sample is heated to determine if the ratio meets a predetermined standard. Such a standard might provide, for example, that the net weight of the container before heating might be 3–5% greater than the net weight of the container after the sample is heated. The computer may adjust an item of equipment that processes the components of the product, such as metering system 208 or the discharge openings of bins 220, 222, 224 and 226, or the speed of conveyor 228 to adjust the rate at which asphalt cement or aggregate materials are introduced into drum mixer 204, if the ratio of the weight of the sample of the product before it is heated to the weight of the sample after it is heated does not meet the predetermined standard. For example, if the ratio of the weight of the asphalt binder component to the total weight of the sample is too low, the rate at which asphalt cement is introduced into mixer 204 may be increased or the rate at which aggregate materials are introduced into the mixer may be decreased. Other adjustments, such as the operating rate of the mixer itself, may also be made.

Referring again to FIG. 1, conveyor 300 is provided to transport the components of the product remaining in the oven after the sample is heated to gradation assembly 310. Of course, a bucket elevator or, depending on the relative altitude of the oven assembly and gradation assembly, a chute or another type of transport device known to those having ordinary skill in the art to which the invention relates, may also be employed to convey the aggregate materials from the oven to the gradation assembly.

As shown in FIG. 10, preferred plant 10 includes aggregate sampler 232 which is mounted to conveyor 230 and adapted to obtain a sample therefrom during operation of the conveyor. Preferably, sampler 232 is an ACCUSWEEP brand of belt sampler manufactured by Astec, Inc. of Chattanooga, Tenn., although other belt samplers as are known to those having ordinary skill in the art to which the invention relates may also be employed. Preferably, the aggregate sampler is adapted to obtain a sample of approximately 40 pounds from conveyor 230. As shown in FIGS. 10 and 11, the sampler deposits a sample of aggregate materials into material inlet 260 of aggregate sample dryer 234 through chute 262 (not shown in FIG. 1). Inlet 260 may optionally include a resistance heater (not shown) mounted to its surface to begin the heating process to volatilize and drive off the moisture and other volatile components in the sample obtained by aggregate sampler 232. Beneath and in communication with the material inlet is heating chamber 264, which is preferably suspended from support frame 266 by a plurality of load cells 268. A heat source is provided to heat the aggregate material in the heating chamber to volatilize the moisture and other volatile components therein. Such volatile components may include asphalt binder, especially if the aggregate material is recycled asphalt. Preferably, the heat source is provided in the form of heater coil 270 which is attached to a source of air (not shown) so that heated air may be supplied through the coil into the heating chamber. Computer 238, in combination with load cells 270, may be employed to weigh the aggregate material in the heating chamber as it is heated. Typically, it has been found that 10–15 minutes are required to volatilize substantially all of the moisture from a forty-pound sample of virgin aggregate materials such as crushed limestone. As much as 30 minutes or more may be required to volatilize the volatile components from a forty-pound sample of recycled asphalt. As the heating progresses, computer 238 may be employed to monitor the change of weight of the aggregate sample in the heating chamber and to determine when a predetermined time, such as five minutes, has elapsed with no change in the weight of the heating chamber and its contents. When no change in weight is detected for a predetermined period of time, it may be assumed that the volatile components in the sample have been removed. At this point, hydraulic actuator 272 may be employed to open the gate (not shown) at the bottom of the heating chamber to drop the sample through discharge chute 274 and onto conveyor 236 (shown in FIG. 1).

Referring again to FIG. 1, conveyor 236 is provided to transport the components of the aggregate sample discharged from the heating chamber to gradation assembly 310. Of course, a bucket elevator or, depending on the relative separation of the aggregate sample dryer and the gradation assembly, a chute or another type of transport device known to those having ordinary skill in the art to which the invention relates, may also be employed to convey the aggregate materials from the aggregate sample dryer to the gradation assembly.

Figure 12:
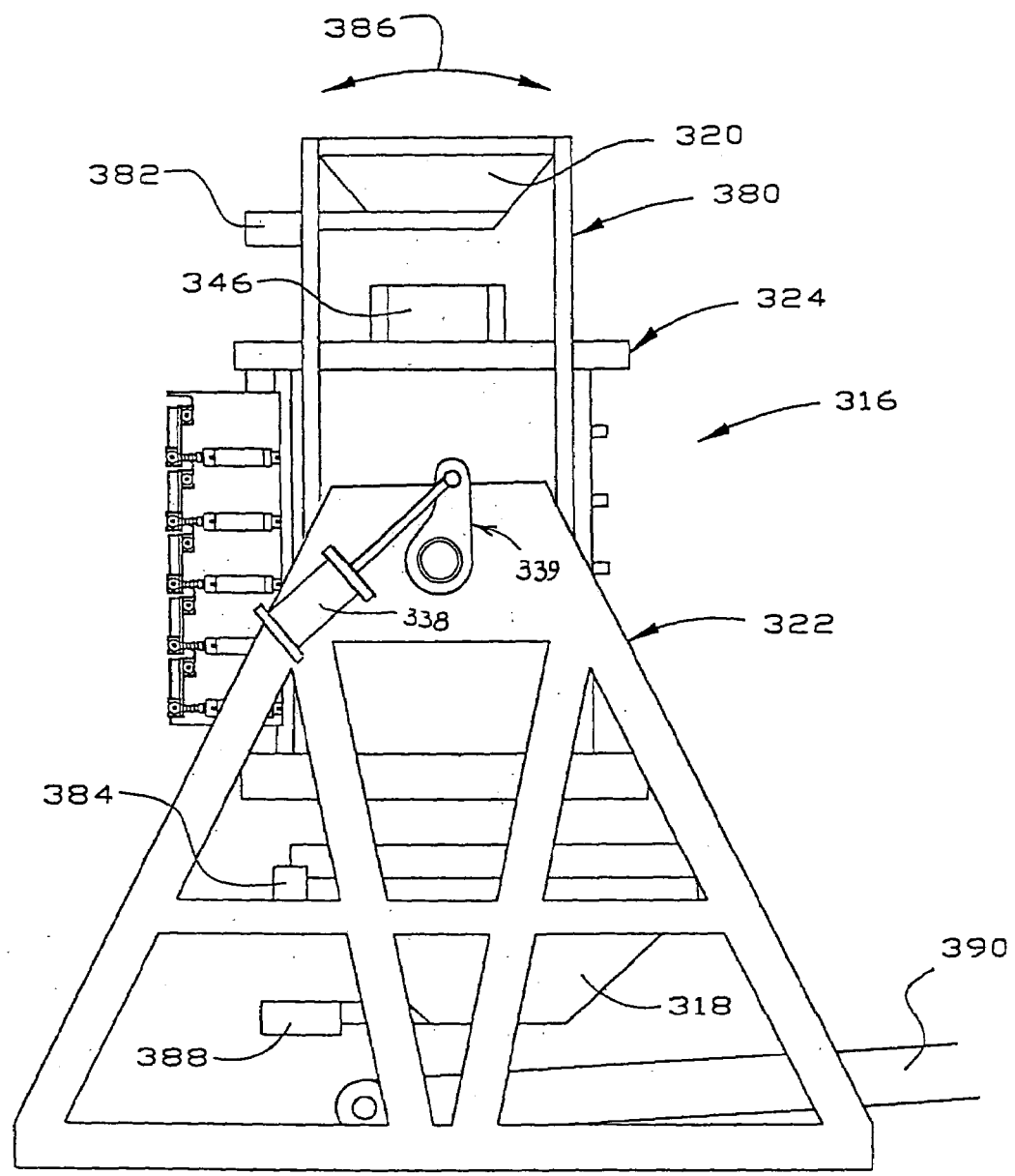
FIG. 12 is a side view of a portion of the preferred embodiment of the gradation assembly of the invention, showing the supporting frame for the gradation screens in a first position in which the screens are disposed generally horizontally in the stack.
Figure 13:
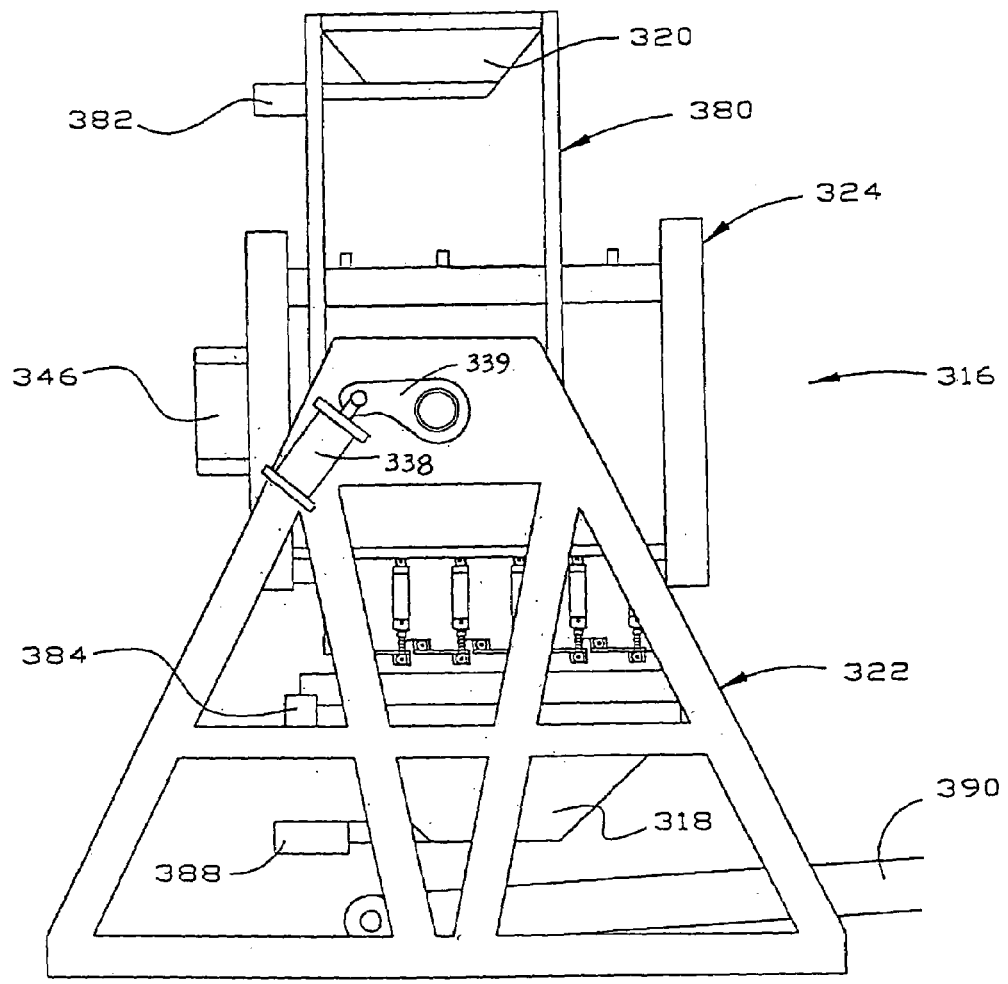
FIG. 13 is a side view of the apparatus of FIG. 12, showing the supporting frame for the gradation screens in a second position in which the screens are disposed generally vertically in the stack.
Figure 14:
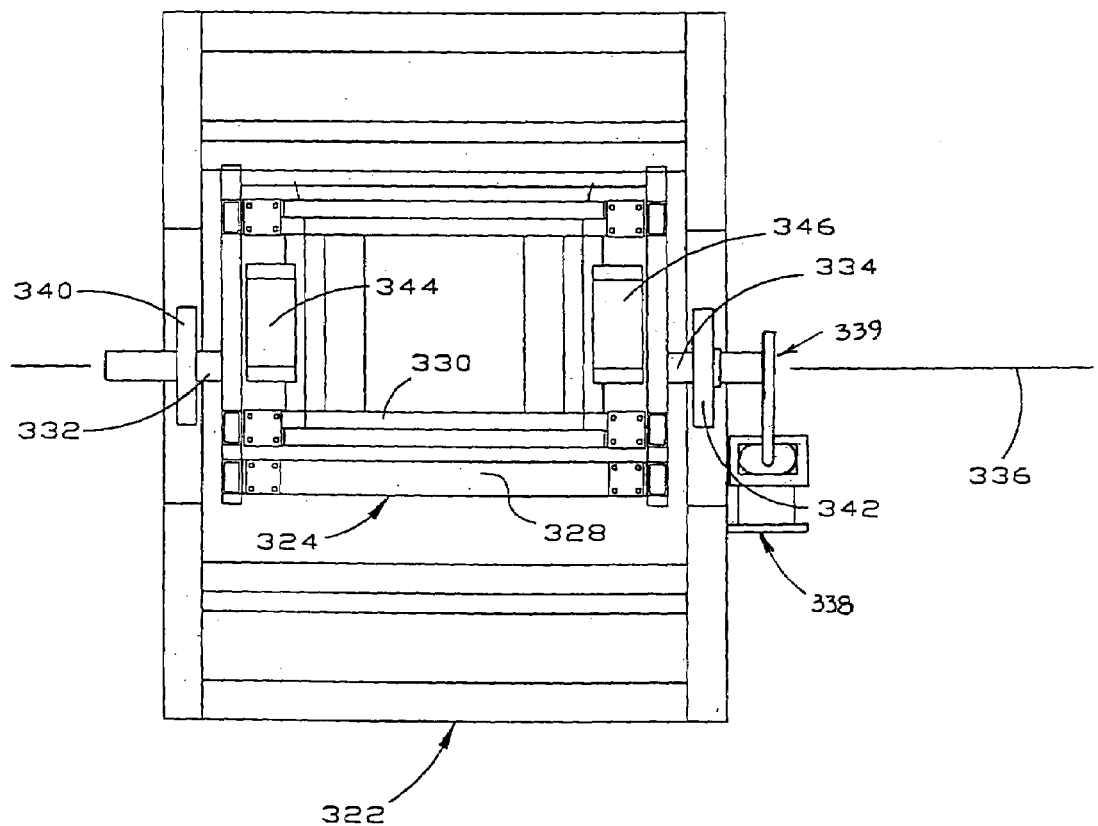
FIG. 14 is a top view of a portion of the apparatus of FIG. 13, with the metering hopper, weighing pan, screens and associated components deleted.
Figure 15:
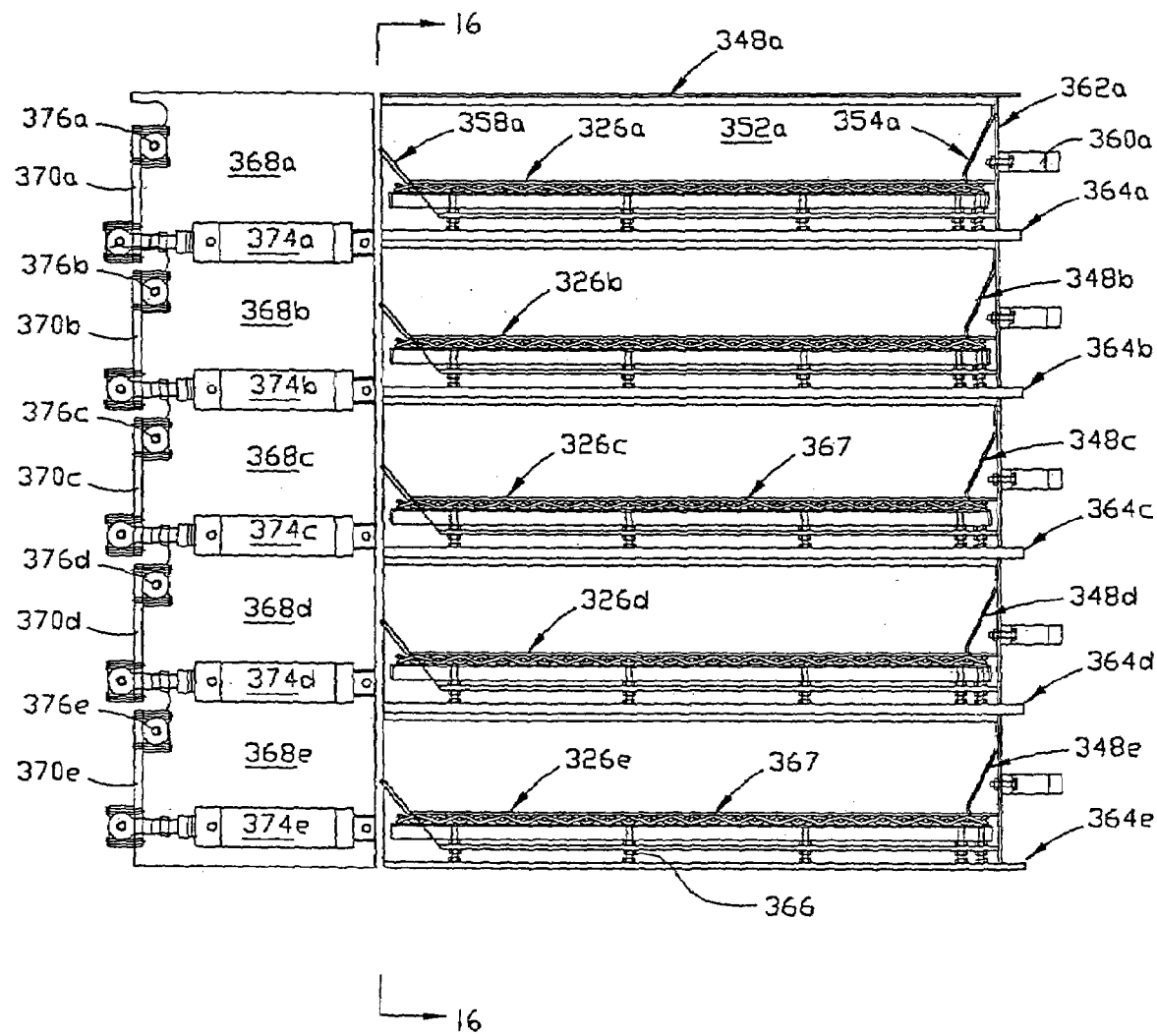
FIG. 15 is a side view of the screen assembly of the apparatus of FIG. 12, showing the screens and associated trays and chutes in a first position in which the screens are disposed generally horizontally in the stack.
Figure 16:
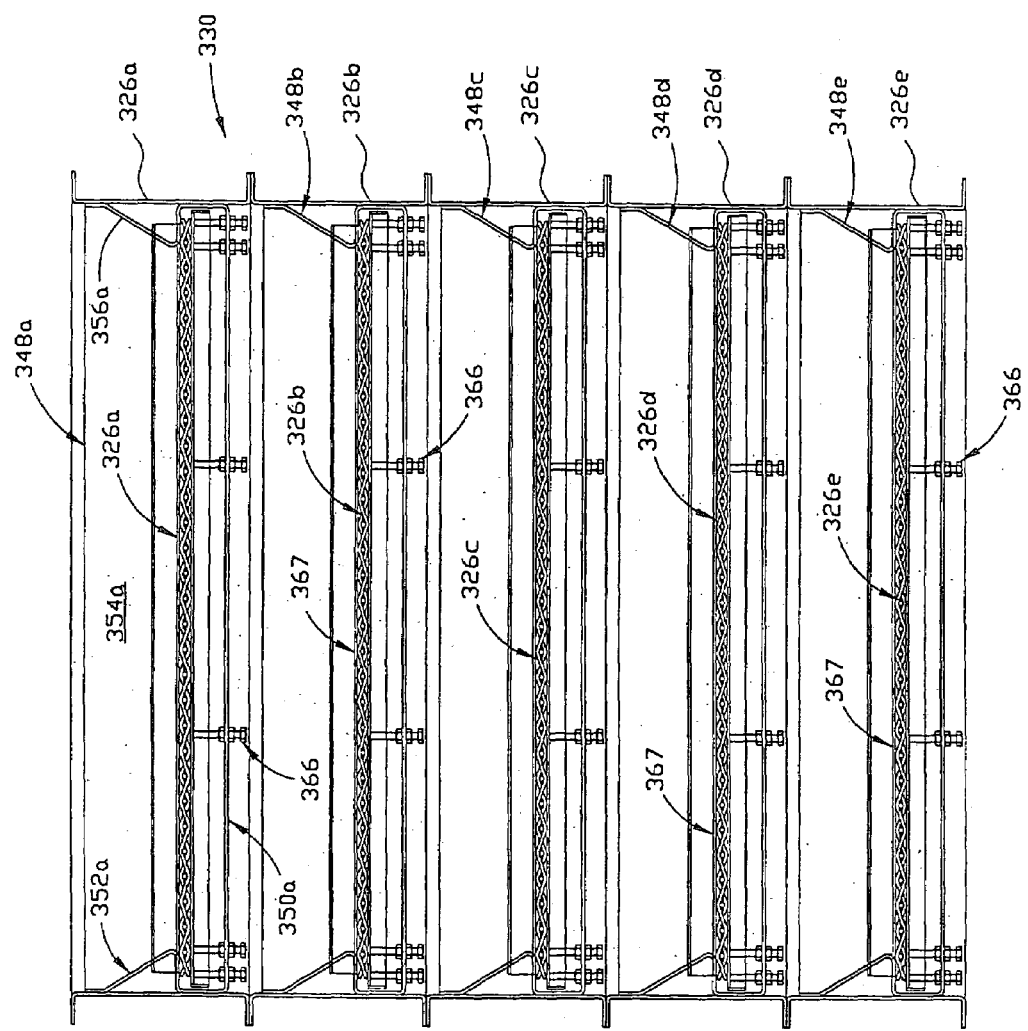
FIG. 16 is an end view of a portion of the screen assembly of the apparatus of FIG. 15, taken along the line 16—16 of FIG. 15.
Figure 17:
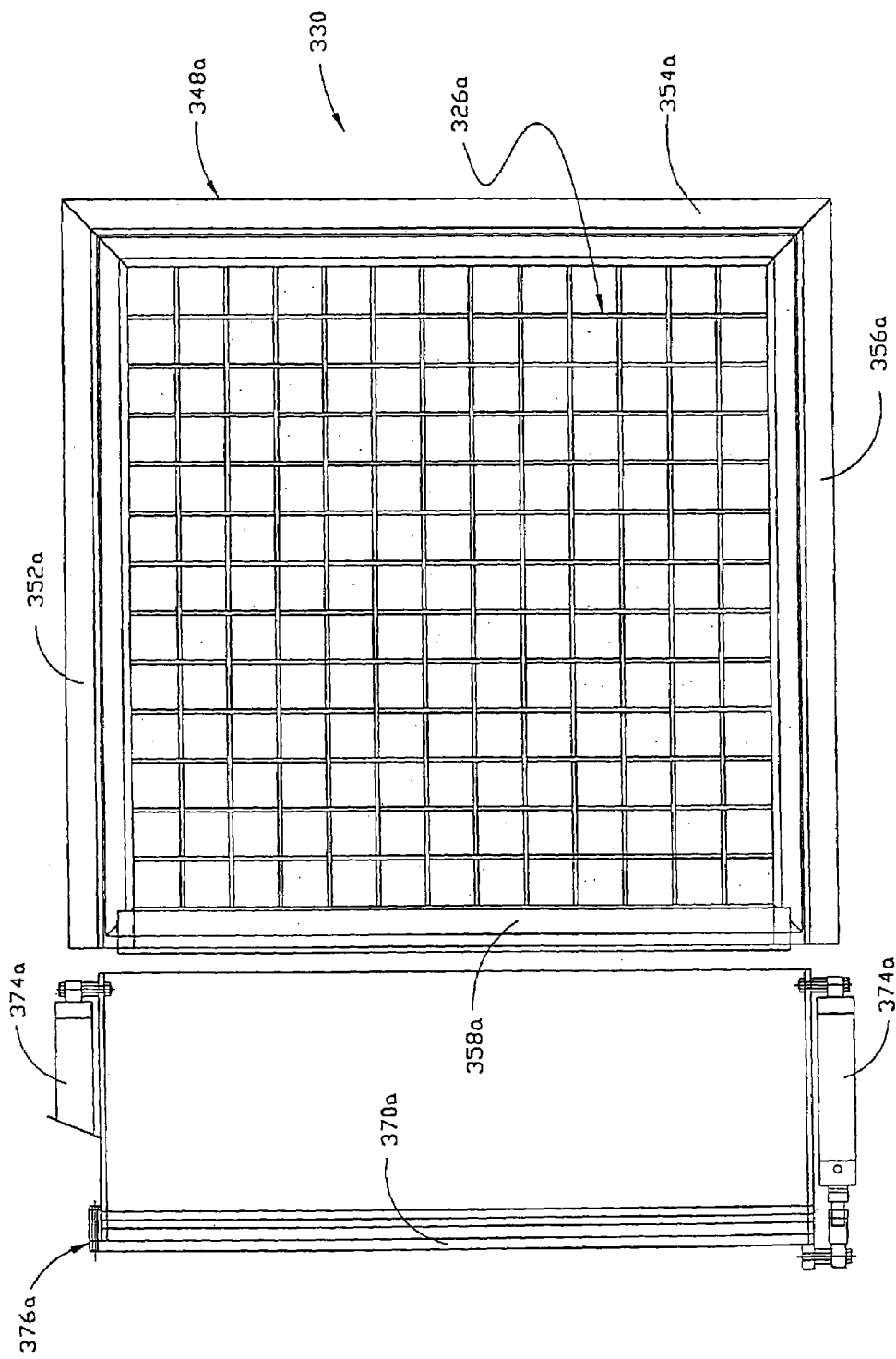
FIG. 17 is a top view of the apparatus of FIG. 15.

Referring now to FIGS. 12, 13 and 14, gradation assembly 310 includes weighing pan 318 and metering hopper 320, which are mounted on support base 322. In the alternative, the weighing pan may be mounted on an entirely separate support (not shown) to isolate it from the remainder of the assembly. The gradation assembly also includes frame 324 which is adapted to support a plurality of gradation screens in a generally horizontal attitude (as shown in FIGS. 12, 15 and 16) in a stacked arrangement. The screens are arranged with the screen having the largest screen openings at the top of the stack and each of the other screens in the stack having screen openings that are smaller than those of the screen immediately above it in the stack. Various screen sizes may be utilized, depending on the desired particle sizes (or particle size ranges) of aggregate materials in the product. As shown in FIGS. 15–17, screens 326a, 326b, 326c, 326d and 326e are mounted in a stacked arrangement in the gradation assembly. Although five such screens are illustrated in the drawings, any number of screens greater than one may be employed in connection with the invention, depending primarily on the number of different particle sizes (or particle size ranges) of aggregate materials in the product.

Preferably, frame 324 is comprised of an outer frame portion 328 and an inner frame portion 330 (best shown in FIG. 12) in which the gradation screens are mounted. Frame 324 is rotatable from a first frame position (illustrated in FIG. 12), in which the screens are disposed in a generally horizontal attitude, to a second frame position (shown in FIG. 13), in which the screens are disposed generally vertically. Although it is preferred that the screens in the first position be oriented precisely horizontally with respect to the ground, any angle of orientation that will permit the passage of material that is smaller than the openings in a screen through such screen to the screen below it in the stack may be encompassed by the term "generally horizontal". Furthermore, it is not necessary that all of the screens be oriented at precisely the same "generally horizontal" attitude, so long as the condition described above is met with respect to each screen in the stack. Finally, although it is preferred that the screens in the second position be oriented precisely vertically with respect to the ground, any angle of orientation that will facilitate the discharge of material that is retained on the screens into the associated chutes (as subsequently described in more detail) may be encompassed by the term "generally vertically", and it is not necessary that all of the screens be oriented at precisely the same "generally vertical" attitude, so long as the condition described above is met with respect to each screen in the stack.

A pair of stub shafts 332 and 334 define an axis of rotation 336 (see FIG. 14) about which support frame 324 is rotated by operation of gearmotor 337 (see FIG. 1), or more preferably, hydraulic actuator 338 and crank 339 (see FIGS. 12–14). Preferably, axis 336 intersects the center of mass of frame 324 and its components. One end of each of the stub shafts is preferably welded to the side of outer frame portion 328 of support frame 324, and the shafts are adapted for rotation in pillow block bearings 340 and 342 which are bolted or otherwise attached to base 322. Shaft 334 may be fitted with a brake to permit locking of support frame 324 in either the first frame position, in which the screens are disposed generally horizontally, or the second frame position, in which the screens are disposed generally vertically. A pair of vibrating motors 344 and 346, comprising motors having eccentrically mounted weights on a rotating shaft or other vibrating means, are mounted on inner frame portion 330. The outer frame portion 328 is preferably isolated from the vibrations imposed on inner frame portion 330 by a plurality of rubber cushions or other elastomeric isolators (not shown).

Referring now to FIGS. 15–17, preferred inner frame portion 330 (shown in FIG. 14) includes a plurality of trays in which the screens are mounted in a stacked arrangement. Thus, screen 326a is mounted in tray 348a at the top of the stacked arrangement when the screens are in the first (generally horizontal) screen position. Similarly, screen 326b is mounted in tray 348b just beneath screen 326a, screen 326c is mounted in tray 348c just beneath screen 326b, screen 326d is mounted in tray 348d just beneath screen 326c and screen 326e is mounted in tray 348e just beneath screen 326d. In the alternative, tray 348e and screen 326e may be replaced by a tray having a solid floor (not shown) that is adapted to collect fine material that passes through all of the screens.

Each tray of the preferred embodiment of the invention is essentially identical to each other tray, as shown in FIGS. 15–17. Thus, for example, tray 348a is comprised of peripheral floor 350a, three aggregate retaining walls 352a, 354a and 356a, and an aggregate releasing wall 358a, as shown in FIGS. 13 and 14. The peripheral floor of each tray supports the peripheral edges of its associated screen, leaving the area beneath the screen cloth of the screen open to permit aggregate material that is small enough to pass through the openings in the screen cloth to drop down to the screen below (when the screens are in the first position). The shape of the tray and the height of its aggregate retaining and aggregate releasing walls are preferably such that aggregate that is too large to pass through the screen mounted therein will be retained within the tray while the screen is being vibrated in the first position. The aggregate releasing wall is preferably sized so that upon rotation of the screen to the second position, aggregate retained on the screen may pass over the aggregate retaining wall and into the associated chute (as hereinafter described).

Figure 18:
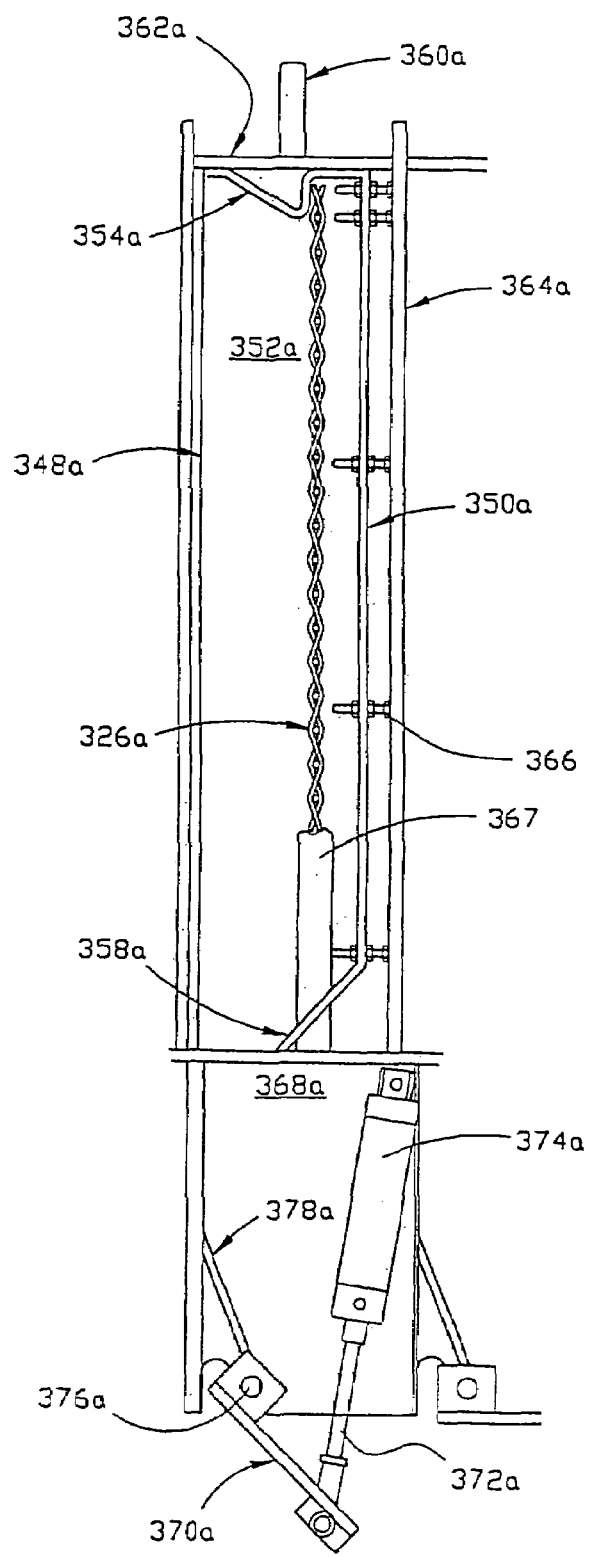
FIG. 18 is a side view of a portion of the screen assembly of FIG. 15, showing a screen and associated tray and chute in a second position in which the screen is disposed generally vertically in the stack, and showing the chute door in an open position.

Access handle 360a (see FIG. 15) is attached to end wall 362a which is located adjacent to aggregate retaining wall 354a and opposite aggregate releasing wall 358a. Similar access handles are attached to trays 326b, 326c, 326d, and 326e. Trays 326a, 326b, 326c, 326d and 326e are supported on peripheral flanges 364a, 364b, 364c, 364d and 364e respectively, which are disposed around the periphery of inner frame portion 330, and bolts 366 are provided to hold the screens securely in place in the trays. Preferably, as shown in FIGS. 15, 17 and 18, the outer peripheries of the screens are bounded by angles 367, and bolts 366 bear against the bottom of the angles to hold the screens securely in place. When it is desired to remove a tray to replace a screen or for another reason, the handle may be grasped and the tray pulled out of the inner frame portion to the right as viewed in FIG. 15.

A chute is provided for each tray and screen assembly in inner frame portion 330 of preferred assembly 310. Thus, as shown in FIG. 15, chute 368a is provided for tray 348a and its associated screen, chute 368b is provided for tray 348b and its associated screen, chute 368c is provided for tray 348c and its associated screen, chute 368d is provided for tray 348d and its associated screen, and chute 368e is provided for tray 348e and its associated screen (or for an alternative tray having a solid floor). Each chute has a door at its end which is pivotally mounted so as to swing open upon extension of a pair of cylinders that are mounted at either side thereof so that material in the chute may be discharged from the chute when frame 324 is in the second position with the screens disposed generally vertically. Such cylinders may be fluid powered, such as, for example, air cylinders. FIG. 18 illustrates the relationship of chute 368a, tray 348a and screen 326a when screen 326a is disposed in the generally vertical (or second) position. As shown therein, chute 368a is provided with door 370a which is actuated by the extension of a pair of cylinder rods 372a (only one of which is shown) from cylinders 374a (see FIG. 17) to pivot open about pivot axis 376a. It is preferred that an inner angled wall 378a be provided within chute 368a to divert material discharged from the chute away from the pivoting hinge (or axis 376a) of door 370a. Chutes 368b, 368c, 368d and 368e are essentially identical to chute 368a. Door 370b of chute 368b may be pivoted about pivot axis 376b to open upon actuation of cylinders 374b (only one of which is shown). Similarly, doors 370c, 370d and 370e of chutes 368c, 368d and 368e respectively may be pivoted about pivot axes 376c, 376d and 376e respectively to open upon actuation of cylinder pairs 374c, 374d and 374e (only one of each pair of which is shown in the drawings). When the screen assembly is rotated to the second position, any material that is retained on a screen (or any material that is retained in a solid floor tray that is substituted for tray 348e and screen 326e) will fall past the aggregate releasing wall of its tray and into its associated chute for subsequent discharge through the chute door.

Referring again to FIG. 1, gradation assembly 310 is preferably controlled by computer 238 and connected to existing control systems on the cold feed proportioning system or other item of equipment. The software utilized by the computer is readily available for industrial control applications. Such software is capable of computing percentage data, compiling statistical data and maintaining historical data. In a preferred embodiment of the invention, computer 238 is connected to control means for the discharge openings of the cold feed bins and to control means for controlling the speed of conveyor 228 in order to adjust the relative proportions of aggregate materials from each of the cold feed bins that are conveyed to drum mixer 204.

To begin operation of gradation assembly 310, frame 324 is placed in a first frame position that is adapted to support the gradation screens in a generally horizontal attitude. A signal from the computer controller or other starting device will actuate a conveyor (conveyor 236 or conveyor 300) to transport aggregate materials (from aggregate sample dryer 234 or oven assembly 110) into metering hopper 320 (FIG. 12), which is mounted on support base 322 by hopper frame 380.

The metering hopper is preferably fitted with cylinder 382 which slowly opens a gate (not shown) in the bottom of the hopper, allowing the sample to drop onto screen 326a at a controlled rate. Preferably, the metering hopper will deposit the sample on the uppermost screen in the stack at a rate within the range of about 40% to about 80% by weight of the total quantity of aggregate material per minute.

Prior to deposit of the aggregate material onto screen 326a (or prior to deposit of any portion of the aggregate material into weighing pan 318, if tray 348e and screen 326e have been replaced by a tray having a solid floor that is adapted to collect fine material that passes through all of the screens), one or more load cells 384 (only one of which is shown) on weighing pan 318 will weigh the pan to obtain a tare (or empty weight). This weight will be recorded and saved by software associated with the controlling computer.

As cylinder 382 is actuated to deposit the sample on the first screen of the gradation assembly, vibrator motors 344 and 346 or other vibrating means are actuated to vibrate the screens in the gradation assembly. Preferably, the vibration is confined to inner frame portion 330 of frame 324 by suitable elastomeric isolators (not shown). The screens may be vibrated in the first position for any suitable length of time. When used in connection with preferred asphalt production plant 10, the screen assembly is preferably vibrated in the first position for about 50 to about 125 seconds, most preferably for about 90 seconds. Preferably, the vibrating motors are adapted to apply vibrations to the screens in a series of frequencies, with the first frequency being adapted to induce resonance in the uppermost screen in the stack and each subsequent frequency being adapted to induce resonance in a screen immediately below the screen in which resonance was previously induced. Thus, as illustrated in the drawings, vibrating motors 344 and 346 will preferably apply vibrations to the gradation assembly at a first frequency adapted to induce resonance in screen 326a for about 10 to about 90 seconds, most preferably for about 60 seconds. Then the vibrating motors will change the frequency at which vibrations are applied to a second frequency that is adapted to induce resonance in screen 326b for a period of time similar to that at which vibrations were applied at the resonance frequency of screen 326a. Then the vibrating motors will change the frequency at which vibrations are applied to a third frequency that is adapted to induce resonance in screen 326c for a period of time similar to that at which vibrations were applied at the resonance frequencies of screens 326a and 326b. Then the vibrating motors will change the frequency at which vibrations are applied to a fourth frequency that is adapted to induce resonance in screen 326d for a period of time similar to that at which vibrations were applied at the resonance frequencies of screens 326a, 326b and 326c. Finally, the vibrating motors will change the frequency at which vibrations are applied to a fifth frequency that is adapted to induce resonance in screen 326e for a period of time similar to that at which vibrations were applied at the resonance frequencies of screens 326a, 326b, 326c and 326d. Of course, depending on the nature of the aggregate product that is being processed by the gradation assembly, it may be desirable to vibrate certain screens at their resonance frequencies for a period of time that is different from that at which certain other screens are vibrated at their resonance frequencies.

It is also preferred that during vibration of the screens in the first position, gearmotor 337 or actuator 338 be actuated to rotate shaft 334 first in one direction and then the other in order to rock frame 324 back and forth about pivot axis 336 through an angular displacement, preferably within the range of less than about 20°, as illustrated by arrow 386 of FIG. 12. As the screens are vibrated, aggregate material that is small enough to pass through the openings in the screen cloth at each screen level will pass through and be screened through lower screens in the stack. Material that passes through all five screens (or such other number as may be employed) will fall into weighing pan 318 (or be retained in a solid-floored tray that is substituted for tray 348e and screen 326e). When vibration in the first frame position has been completed, cylinder 382 will be actuated to close the gate in metering hopper 320 and gearmotor 337 or actuator 338 will be actuated to rotate frame 324 from the first position to a second position in which the screens are disposed generally vertically. As frame 324 is rotated to the second position, aggregate material retained on each of the screens (or on a solid-floored tray that is substituted for the lowermost screen) will fall into the chutes associated with the screens.

Preferably, the vibrating motors will be actuated (or will continue to operate) to vibrate the screens while the frame is in the second frame position in order to dislodge any material that is caught in the screens. The screens may be vibrated in the second position for any suitable length of time. When used in connection with preferred asphalt production plant 10, the screen assembly is preferably vibrated in the second position for a period of about 10 to about 60 seconds, most preferably for about 20 seconds for each screen in the assembly. Preferably, the vibrating motors are adapted to apply vibrations to the screens in a series of frequencies, with each such frequency being adapted to induce resonance in one of the screens in the stack. Thus, for example, vibrating motors 344 and 346 may be operated to apply vibrations to the gradation assembly at a first frequency adapted to induce resonance in screen 326a for about 10 to about 60 seconds, most preferably for about 20 seconds. Then the frequency at which vibrations are applied may be changed to a second frequency that is adapted to induce resonance in screen 326b for a period of time similar to that at which vibrations were applied at the resonance frequency of screen 326a. Then the frequency at which vibrations are applied may be changed to a third frequency that is adapted to induce resonance in screen 326c for a period of time similar to that at which vibrations were applied at the resonance frequencies of screens 326a and 326b. Then the frequency at which vibrations are applied may be changed to a fourth frequency that is adapted to induce resonance in screen 326d for a period of time similar to that at which vibrations were applied at the resonance frequencies of screens 326a, 326b and 326c. Finally, the frequency at which vibrations are applied may be changed to a fifth frequency that is adapted to induce resonance in screen 326e for a period of time similar to that at which vibrations were applied at the resonance frequencies of screens 326a, 326b, 326c and 326d. Although the application of vibrations at the resonance frequencies of the various screens in the second position has been described herein in a particular sequence, such vibrations may be applied to the various screens in any order or sequence according to this preferred embodiment of the invention.

After completing vibration of the screens at the second position, the vibrating motors will be shut off, and one or more load cells 384 on weighing pan 318 will weigh the contents of the material in the weighing pan that has passed through all of the screens (unless a solid-floored tray has been substituted for tray 348e and screen 326e). This weight will be recorded and saved by software associated with the controlling computer. Subsequently, cylinders 374a are actuated to open chute door 370a to permit the contents of chute 368a to fall into weighing pan 318. The amount deposited in the pan will be weighed and this weight will be recorded and saved. If material has been previously weighed in the weighing pan, the difference between the previously recorded weight (less the tare weight) immediately prior to discharge of material from chute 368a and the weight (less the tare weight) with the material from chute 368a will be calculated to determine the weight of the material retained on screen 326a and discharged into the weighing pan through chute 368a. Chute door 370a will then be closed by retraction of the cylinder rods of cylinders 374a, and chute door 370b will be opened to permit the contents of chute 368b to fall into weighing pan 318. The amount deposited in the pan will be weighed and this weight will be recorded and saved. The difference between the previously recorded weight (less the tare weight) immediately prior to discharge of material from chute 368b and the weight (less the tare weight) with the material from chute 368b will be calculated to determine the weight of the material retained on screen 326b and discharged into the weighing pan through chute 368b. Chute door 370b will then be closed by retraction of the cylinder rods of cylinders 374b, and chute door 370c will be opened to permit the contents of chute 368c to fall into weighing pan 318. The amount deposited in the pan will be weighed and this weight will be recorded and saved. The difference between the previously recorded weight (less the tare weight) immediately prior to discharge of material from chute 368c and the weight (less the tare weight) with the material from chute 368c will be calculated to determine the weight of the material retained on screen 326c and discharged into the weighing pan through chute 368c. Chute door 370c will then be closed by retraction of the cylinder rods of cylinders 374c, and chute door 370d will be opened to permit the contents of chute 368d to fall into weighing pan 318. The amount deposited in the pan will be weighed and this weight will be recorded and saved. The difference between the previously recorded weight (less the tare weight) immediately prior to discharge of material from chute 368d and the weight (less the tare weight) with the material from chute 368d will be calculated to determine the weight of the material retained on screen 326d and discharged into the weighing pan through chute 368d. Chute door 370d will then be closed by retraction of the cylinder rods of cylinders 374d, and chute door 370e will be opened to permit the contents of chute 368e to fall into weighing pan 318. The amount deposited in the pan will be weighed and this weight will be recorded and saved. The difference between the previously recorded weight (less the tare weight) immediately prior to discharge of material from chute 368e and the weight (less the tare weight) with the material from chute 368e will be calculated to determine the weight of the material retained on screen 326e (or retained by a solid-floor tray that has been substituted for tray 348e and screen 326e) and discharged into the weighing pan through chute 368e. Chute door 370e will then be closed by retraction of the cylinder rods of cylinders 374e.

The order in which the chute doors are opened so that material contained therein may be deposited in the weighing pan is not particularly critical, so long as the system operates to sequentially deposit the aggregate material that is retained on each screen in the weighing pan. After all of the material in the sample has been weighed, the computer will determine the total weight of the sample (by adding all of the amounts that are retained on each of the screens and the amount which passes through all of the screens). The computer will then determine the ratios of the weights of the amounts of the aggregate materials that are retained on each of the screens (or which passes through all of the screens) to the total weight of the sample. A predetermined standard for each such ratio will have been stored in the computer, and the computer will then compare each calculated ratio (of the weight of material retained on a screen or passing through all of the screens) to the predetermined standard for such sized material. If the computer determines that any ratio of the weight of the amount of the aggregate materials that is retained on any of the screens (or which passes through all of the screens) to the total weight of the sample fails to meet the predetermined standard for such screen size, it will adjust the control systems on the cold feed proportioning system or other items of equipment to change the operation of the equipment to bring the weight of the materials retained on the screens (or which passes through all of the screens) within applicable weight ratio standards. In the alternative, the controlling computer, with appropriate software adjustment, may be operated to bypass any given tray position for chute discharge, or to determine one or more ratios based upon a combination of the material discharged through two or more chutes.

After all weight calculations have been made, weighing pan cylinder 388 may be actuated to open a gate (not shown) in the weighing pan to drop the material therein onto the ground or onto a conveyor such as return conveyor 390 (not shown in FIG. 1), which conveyor may be adapted to transport the material to a stockpile or other storage location. The gate is then closed and frame 324 is rotated to the first frame position.

Each of the components of the preferred embodiment of the invention, including the oven assembly, the gradation assembly, the asphalt sample collector, the aggregate sample collector, the aggregate sample dryer and the asphalt binder metering system are preferably controlled by computer 238 and connected to control systems on the cold feed proportioning system, mixer 204 or other items of equipment (such as asphalt flow valve 214) that are used in the manufacture of asphalt. The software utilized by the computer is capable of computing percentage data, compiling statistical data and maintaining historical data.

In operation, the numerous advantages of the invention are evident. The invention permits the user to obtain a sample of an asphalt product from a predetermined location such as the open bed of a truck using the asphalt sample collector. The asphalt sample collector may then transport the sample of the product to the oven assembly where the sample is weighed. Then, the sample is heated in the oven until substantially only the aggregate materials remain. The remaining aggregate materials may then be weighed. The ratio of the weight of the sample before it is heated to the weight of the sample after it is heated may then be determined. Next, the ratio may be compared to a predetermined standard in order to determine if the composition of the sample meets the standard. In the event that the ratio fails to meet the predetermined standard, the rate at which the asphalt binder and/or the aggregate materials are added to mixer 204 may be adjusted to bring the relative proportion of the various components in the product within the desired standard. The invention also permits the user to obtain a sample of aggregate materials from the cold feed conveyor system using the aggregate sampler. The aggregate sample may then be deposited in the aggregate sample dryer and the sample may be heated until the volatile components therein are removed.

Thereafter, the remaining aggregate materials (from the oven assembly or the aggregate sample dryer) may be conveyed to the gradation assembly, and the process of grading the aggregate materials may commence. First, the aggregate materials are deposited on the first screen of the gradation assembly while the frame is in a generally horizontal attitude. Then, the screens are vibrated. Thereafter, the aggregate materials retained on the first screen are deposited in the weighing pan and weighed. Next, the aggregate materials retained on each subsequent screen are sequentially deposited in the weighing pan and weighed until the aggregate materials on each screen have been deposited in the weighing pan and weighed. Then, the ratios of the weight of the aggregate materials retained in each screen to the total weight of the aggregate materials may be calculated. Next, the system may determine whether the ratios calculated in the previous step meet with corresponding predetermined standards. Finally, the system may automatically adjust the operation of the cold feed proportioning system to increase or decrease the relative weight of one or more of the components of the asphalt product if one or more of the weight ratios fails to meet the corresponding predetermined standard.

Although this description contains many specifics, these should not be construed as limiting the scope of the invention but as merely providing illustrations of some of the presently preferred embodiments thereof, as well as the best mode contemplated by the inventors of carrying out the invention. The invention, as described herein, is susceptible to various modifications and adaptations, and the same are intended to be comprehended within the meaning and range of equivalents of the appended claims.

What is claimed is:

1. An asphalt production plant comprising:
  (a) an asphalt binder storage tank;
  (b) a mixer for mixing asphalt binder and aggregate materials;
  (c) an asphalt binder pumping system for conveying asphalt binder to the mixer;
  (d) an asphalt binder metering system for controlling the rate of flow of asphalt binder to the mixer;
  (e) a cold feed proportioning system comprising:
    (1) a plurality of cold feed bins for holding aggregate materials, with each such bin having a discharge opening through which aggregate materials may be discharged;
    (2) a cold feed conveyor system that extends from beneath the discharge openings for the plurality of bins for conveying aggregate materials to the mixer;
    (3) means for adjusting the relative proportions of aggregate materials from each of the cold feed bins that are conveyed to the mixer;
  (f) an aggregate sample dryer for removing volatile components from a sample of aggregate materials;
  (g) an aggregate sampler for obtaining a sample of aggregate material from the cold feed conveyor system and depositing such material in the aggregate sample dryer.

2. The asphalt production plant of claim 1, wherein the aggregate sample dryer comprises:
  (a) a material inlet that is adapted to receive a sample of aggregate material;
  (b) a heating chamber that is in communication with the material inlet;
  (c) a heat source for heating the aggregate material in the heating chamber to volatilize the volatile components therein;
  (d) means for weighing the aggregate material in the heating chamber as it is heated;
  (e) means for determining when the weight of the aggregate material in the heating chamber has not changed for a predetermined period of time.

3. The asphalt production plant of claim 1 wherein the means for adjusting the relative proportions of aggregate materials from each of the cold feed bins that are conveyed to the mixer comprises means for adjusting the discharge openings of the cold feed bins.

4. The asphalt production plant of claim 1 wherein the means for adjusting the relative proportions of aggregate materials from each of the cold feed bins that are conveyed to the mixer comprises a variable speed feeder conveyor and means for adjusting the speed of such feeder conveyor.

5. The asphalt production plant of claim 1:
  (a) wherein the asphalt binder metering system is adapted to measure the volume of a flow of asphalt binder from the asphalt binder storage tank; and
  (b) which includes:
    (i) an asphalt binder calibration tank;
    (ii) means for pumping a measured volume of asphalt binder from the asphalt binder storage tank into the asphalt binder calibration tank;
    (iii) means for determining the weight of the measured volume of asphalt binder that has been pumped into the asphalt binder calibration tank;
    (iv) means for converting the weight of the measured volume of asphalt binder that has been pumped into the asphalt binder calibration tank to a calculated volume;
    (v) means for calibrating the asphalt binder metering system if the calculated volume of asphalt binder in the calibration tank is not equal to the measured volume.

6. The asphalt production plant of claim 5 wherein the means for determining the weight of the measured volume of asphalt binder that has been pumped into the asphalt binder calibration tank comprises one or more load cells which are adapted to weigh the calibration tank and its contents.

7. The asphalt production plant of claim 1, which includes:
(a) a gradation assembly comprising:
(1) a base;
(2) a plurality of gradation screens;
(3) a frame that is rotatably mounted on the base and adapted to support the gradation screens in a first frame position in which the screens are disposed in a generally horizontal attitude in a stacked arrangement whereby each screen in the stack has screen openings that are smaller than those of the screen immediately above it in the stack, and in a second frame position in which the screens are disposed generally vertically;
(4) means for vibrating the screens while the frame is in the first frame position;
(b) means for conveying a sample of aggregate material to the gradation assembly;
(c) a weighing pan that is adapted to determine the weight of aggregate materials;
(d) means for sequentially depositing the aggregate materials that are retained on each screen, or that pass through all of the screens, in the weighing pan;
(e) means for determining the ratios of the weights of the amounts of the aggregate materials that are retained on each of the screens or that pass through all of the screens to the total weight of the aggregate materials;
(f) means for determining if each of the ratios of the weights of the amounts of the aggregate materials that are retained on each of the screens or that pass through all of the screens to the total weight of the aggregate materials meets a predetermined standard;
(g) means for adjusting the relative proportions of aggregate materials from each of the cold feed bins that are conveyed to the mixer if the ratio of the weight of the aggregate materials that are retained on any of the screens or that pass through all of the screens to the total weight of the aggregate materials fails to meet the predetermined standard.

8. The asphalt production plant of claim 7 wherein the means for vibrating the screens applies vibrations in a series of frequencies, with said first frequency being applied to induce resonance in the uppermost screen in the stack and each subsequent frequency being applied to induce resonance in a screen immediately below the screen in which resonance was previously induced.

9. The asphalt production plant of claim 7 wherein the gradation assembly includes means for rotating the frame from the first frame position to the second frame position.

10. The asphalt production plant of claim 7 which includes means for vibrating the screens while the frame is in the second frame position by applying vibrations at a predetermined resonance frequency to each of the screens, with each such frequency being applied to induce resonance in one of the screens.

11. The asphalt production plant of claim 7 which includes an actuating cylinder which is operatively connected to the frame and adapted for:
(a) rocking the frame through an angular displacement of less than about 20° while said frame is in the first frame position and during vibration; and
(b) rotating the frame from the first frame position to the second frame position.

12. The asphalt production plant of claim 7 which includes a metering hopper for receiving the sample of aggregate materials and depositing the sample on the uppermost screen in the stack at a controlled rate.

13. The asphalt production plant of claim 7 which includes an oven assembly comprising:
(a) a container defining an interior space, said container having a receiving end for receiving a sample of an asphalt product and a closed end opposite said receiving end;
(b) a heat source for heating the sample of the asphalt product in the container to remove the asphalt binder therefrom;
(c) a weighing mechanism for determining the net weight of the container;
(d) means for determining the ratio of the net weight of the container before the sample is heated to the net weight of the container after the sample is heated;
(e) means for determining if the ratio of the net weight of the container before the sample is heated to the net weight of the container after the sample is heated meets a predetermined standard;
(f) means for transporting the aggregate materials remaining in the oven after the sample is heated to the gradation assembly.

14. The asphalt production plant of claim 13 wherein the oven assembly includes a door that is adapted to move between an open position which exposes the interior space of the container and a closed position which substantially closes the receiving end.

15. The asphalt production plant of claim 13 which includes a mechanism for rotating the container of the oven assembly about a longitudinal axis.

16. The asphalt production plant of claim 13 which includes a mechanism for tilting the container of the oven assembly between an upright position wherein the receiving end is above the closed end and a dumping position wherein at least a portion of the receiving end is below at least a portion of the closed end.

17. The asphalt production plant of claim 13 wherein the mechanism is adapted to tilt the container of the oven assembly approximately 180° between the upright position and the dumping position.

18. The asphalt production plant of claim 13 which includes means for adjusting the rate of flow of asphalt binder to the mixer if the ratio of the weight of the asphalt binder of the asphalt product in the sample to the total weight of the sample fails to meet a predetermined standard.

19. The asphalt production plant of claim 13 which includes an asphalt sample collector comprising:
(a) a support frame having a first frame end and a second frame end;
(b) a pair of guide plates which are attached to the first frame end of the support frame, said guide plates being spaced apart so as to define a collection space therebetween, at least one of said guide plates being provided with a track that extends generally along the periphery of the collection space;
(c) a flexible closing plate which is disposed between the guide plates and adapted for sliding engagement with the track so that the closing plate may be moved between an open position which exposes the collection space and a closed position which encloses the collection space;
(d) means for sliding the closing plate between an open position which exposes the collection space and a closed position which encloses the collection space.

20. The asphalt production plant of claim 19 which includes an asphalt sample conveyor assembly to which the sample collector is mounted to retrieve a sample of the asphalt product from a truck having an open bed and to convey the sample to the container of the oven assembly, said asphalt sample conveyor assembly comprising:
  (a) an assembly frame which includes an overhead rail that is suspended over and adjacent to a truck zone into which the truck has been driven;
  (b) a carriage which is adapted to ride on the overhead rail between a first position for depositing a sample into the container of the oven assembly that is located adjacent to the truck zone and at least one sampling position over the truck zone;
  (c) means for moving the carriage between the first position and at least one sampling position over the truck zone;
  (d) an elongate extension which is attached to the second end of the support frame;
  (e) a boom to which the elongate extension is mounted in sliding engagement therewith;
  (f) means for moving the elongate extension from a retracted position to an extended position for inserting the sample collector into the asphalt material in the truck.

* * * * *